(12) United States Patent
Stanford et al.

(10) Patent No.: US 6,840,950 B2
(45) Date of Patent: Jan. 11, 2005

(54) LOW PROFILE EMBOLI CAPTURE DEVICE

(75) Inventors: Ulf Harry Stanford, Incline Village, NV (US); Yem Chin, Burlington, MA (US); Sheng-Ping Zhong, Northborough, MA (US); John Griego, Blackstone, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 242 days.

(21) Appl. No.: 09/789,332

(22) Filed: Feb. 20, 2001

(65) Prior Publication Data

US 2002/0115942 A1 Aug. 22, 2002

(51) Int. Cl.[7] .......................... A61M 29/00; A61B 5/00; A61F 2/06
(52) U.S. Cl. ...................... 606/200; 600/585; 623/1.12
(58) Field of Search ............................... 600/434, 435, 600/585; 606/114, 159, 195, 198, 200, 192; 623/1–1.54

(56) References Cited

U.S. PATENT DOCUMENTS

| | | |
|---|---|---|
| 3,472,230 A | 10/1969 | Fogarty |
| 3,537,451 A | 11/1970 | Murray et al. |
| 3,952,747 A | 4/1976 | Kimmell, Jr. |
| 3,975,350 A | 8/1976 | Hudgin et al. |
| 3,996,938 A | 12/1976 | Clark, III |
| 4,046,150 A | 9/1977 | Schwartz et al. |
| 4,324,262 A | 4/1982 | Hall |
| 4,425,908 A | 1/1984 | Simon |
| 4,475,972 A | 10/1984 | Wong |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,871,358 A | 10/1989 | Gold |
| 4,873,978 A | 10/1989 | Ginsburg |

(List continued on next page.)

FOREIGN PATENT DOCUMENTS

| | | |
|---|---|---|
| DE | 28 21 048 | 7/1980 |
| DE | 34 17 738 | 11/1985 |

(List continued on next page.)

OTHER PUBLICATIONS

"Atherosclerotic Disease of the Aortic Arch as a Risk Factor of Recurrent Ischemic Stroke," The New England Journal of Medicine, pp. 1216–1221 (May 1996).

(List continued on next page.)

*Primary Examiner*—Eric F. Winakur
(74) *Attorney, Agent, or Firm*—Crompton, Seager & Tufte LLC

(57) ABSTRACT

A low profile emboli capture device is provided for use in angioplasty and other intravascular procedures. A standard guidewire is utilized having a reduced cross-sectional area formed near its distal end. A filter and self-expanding stent are packaged on the reduced cross-sectional area of the guidewire. A movable sleeve extends over the guidewire and holds the self-expanding stent and filter in their retracted positions while the device is being positioned in the artery. The sheath is moved relative to the self-expanding stent and filter, whereupon the self-expanding stent and filter become deployed.

13 Claims, 37 Drawing Sheets

U.S. PATENT DOCUMENTS

| | | |
|---|---|---|
| 4,921,478 A | 5/1990 | Solano et al. |
| 4,921,484 A | 5/1990 | Hillstead |
| 4,926,858 A | 5/1990 | Giffort, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,163,951 A | 11/1992 | Pinchuk et al. |
| 5,224,953 A | 7/1993 | Morgentaler |
| 5,225,196 A * | 7/1993 | Robinson .................... 424/427 |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,547 A | 12/1999 | Nakao et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,277,139 B1 * | 8/2001 | Levinson et al. ........... 606/200 |
| 6,346,116 B1 * | 2/2002 | Brokks et al. .............. 606/200 |
| 6,355,051 B1 * | 3/2002 | Sisskind et al. ............ 606/200 |
| 6,361,545 B1 * | 3/2002 | Macoviak et al. .......... 606/200 |
| 6,361,546 B1 * | 3/2002 | Khosravi .................... 606/200 |
| 6,391,044 B1 * | 5/2002 | Yadav et al. ................ 600/200 |
| 6,540,722 B1 * | 4/2003 | Boyle et al. ................ 606/200 |

FOREIGN PATENT DOCUMENTS

| | | |
|---|---|---|
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 0 934 729 | 8/1999 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |

| | | |
|---|---|---|
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1–12 (Mar. 1996).

"Protruding Atheromas in the Thoracic Aortic and Systemic Embolization," pp. 423–427 American College of Physicians (1991).

"Recognition and Embolic Potential of Intraaortic Atherosclerotic Debris," American College of Cardiology (Jan. 1991).

Cragg, Andrew et al., "A New Percutaneous Vena Cava Filger," *AJR, 141*:601–604 (Sep. 1983).

Cragg, Andrew et al., "Nonsurgical Placement of Arterial Endoprosthesis: A New Technique Using Nitinol Wire," *AJR*, pp. 261–263 (Apr. 1983).

Diethrich et al., "Percutaneous Techniques for Endoluminal Carotid Interventions," *J. Endovase. Surg.*, 3:182–202 (1996).

Fadali, A. Moneim, "A filtering device for the prevention of particulate embolization during the course of cardiac surgery," *Surgery, 64*(3):634–639 (Sep. 1968).

Haissaguerre et al., "Spontaneous Initiation of Atrial Fibrillation by Ectopic Beats Originating in the Pulmonary Veins," *The New England Journal of Medicine, 339*(10):659–666 (Sep. 1988).

Jordan, Jr. et al., "Microemboli Detected by Transcranial Doppler Monitoring . . . ," Cardiovascular Surgery, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," *Laboratory Investigation, 69*(4):772–774 (Apr. 1984).

Marache et al., "Percutaneous Transluminal Venous Angioplasty . . . ," *American Heart Journal, 125*(2 Pt 1):362–366 (Feb. 1993).

Mazur et al., "Directional Atherectomy with the Omnicath™: A Unique New Catheter System," *Catheterization and Cardiovascular Diagnosis, 31*:17–84 (1994).

Moussa, MD, Issaam "Stents Don't Require Systemic Anticoagulation . . . But the Technique (and Results) Must be Optimal," *Journal of Invasive Cardiol., 8*(E):3E–7E, (1996).

Nakanishi et al., "Catheter Intervention to Venous System Using Expandable Metallic Stents," *Rinsho Kyobu Geka, 14*(2):English Abstract Only (Apr. 1994).

Onal et al., "Primary Stenting for Complex Atherosclerotic Plaques in Aortic and Iliac Stenoses," *Cardiovascular & Interventional Radiology, 21*(5):386–392 (1998).

Theron et al., "New Triple Coaxial Catheter System for Carotid Angioplasty with Cerebral Protection," *American Journal of Neuroradiology, 11*:869–874 (1990).

Tunick et al., "Protruding atherosclerotic plaque in the aortic archo f patients with systemic embolization: A new finding seen by transesophageal echocardiography," *American Heart Journal 120*(3):658–660 (Sep. 1990).

Waksman et al., "Distal Embolization is Common After Directional Atherectomy . . . ," *American Heart Journal, 129*(3):430–435 (1995).

Wholey, Mark H. et al., PTA and Stents in the Treatment of Extracranial Circulation, *The Journal of Invasive Cardiology, 8*(E):25E–30E (1996).

* cited by examiner

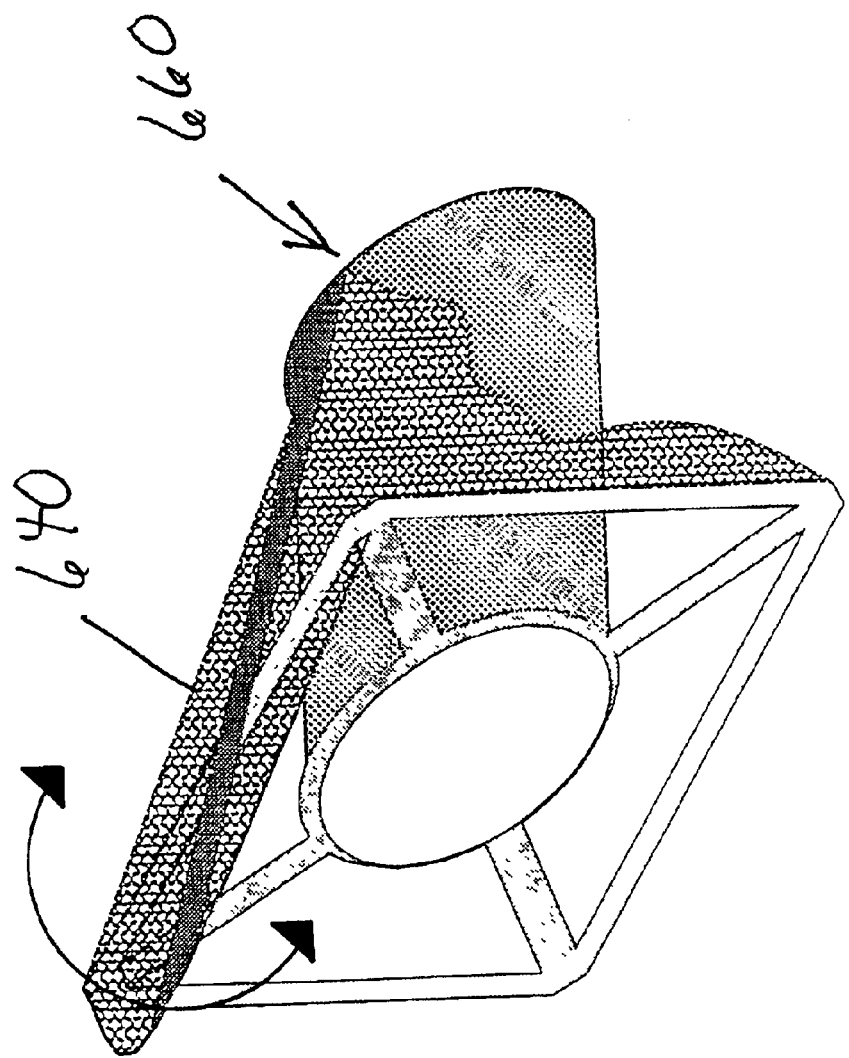

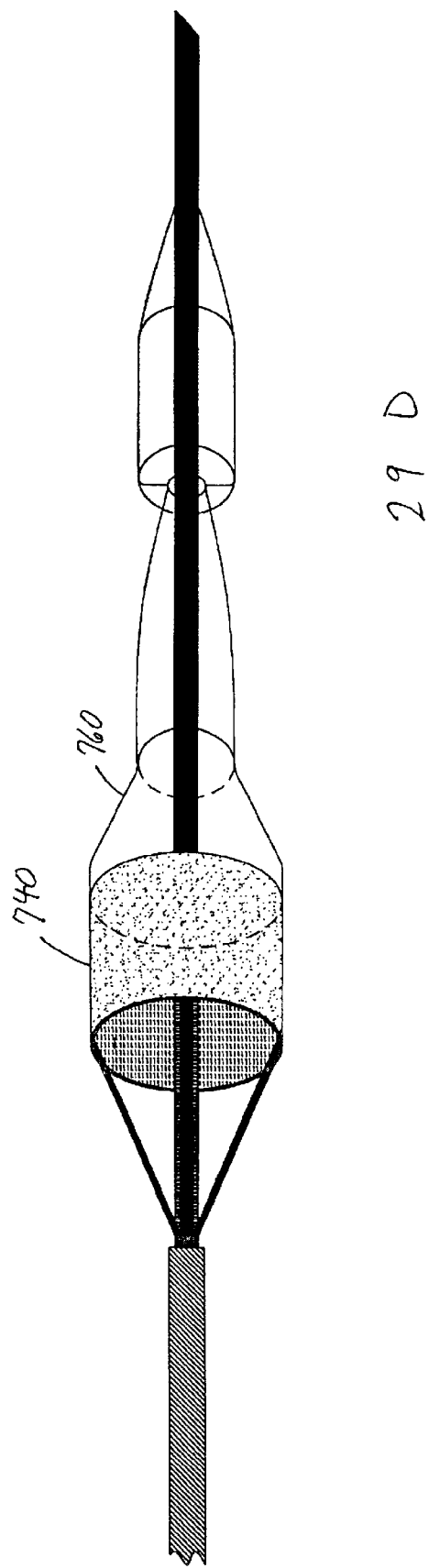

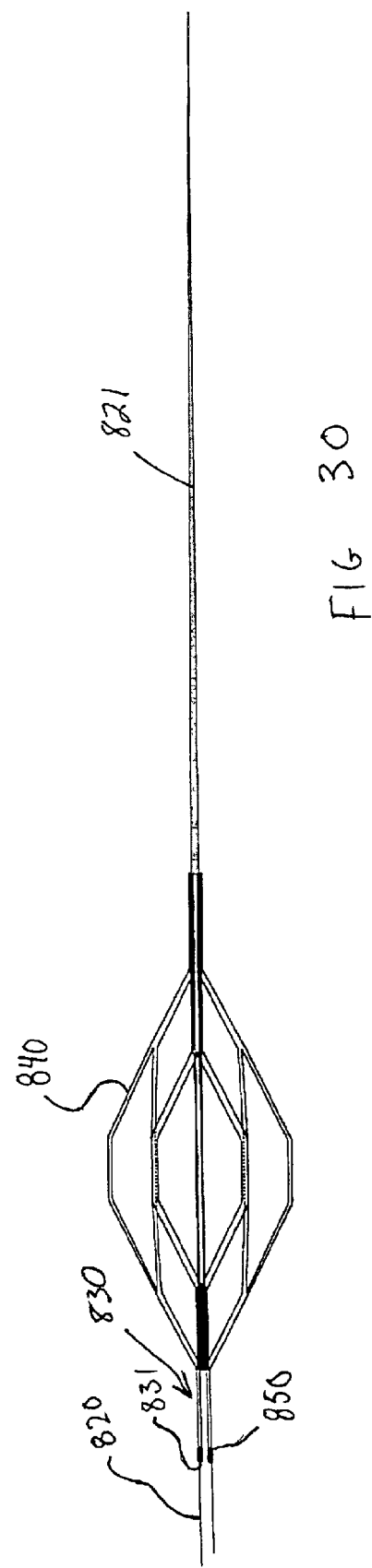

LOW PROFILE EMBOLI CAPTURE DEVICE

BACKGROUND AND BRIEF SUMMARY OF THE INVENTION

The present invention relates generally to an emboli capture device for use in conjunction with angioplasty and other intravascular surgeries. More particularly, the present invention provides a low profile emboli capture device (i.e. approximately 0.020 inch diameter or less in its retracted position) capable of being used in smaller diameter blood vessels than prior art emboli capture devices, as well as reducing the risk of dislodging plaque in larger vessels. The present invention provides an emboli capture device carried by a standard guidewire; a catheter is not required to insert and deploy the emboli capture device. The invention is capable of use in carotid angioplasty without occluding blood flow to the brain, and can be used in saphenous vein grafts, native coronary arteries and arteries as small as 1 mm. diameter.

As angioplasty and other intravascular surgical procedures progress, it becomes increasingly important to be able to use an emboli capture device in smaller and smaller arteries, requiring the use of lower profile devices.

In accordance with the present invention, an emboli capture device is provided which in its preferred form includes three main components that cooperate with a standard guidewire; a self-expanding stent (or other expansion means), a filter and a sleeve. The filter and self-expanding stent in the preferred embodiment are carried directly on a reduced cross-sectional mounting region of the guidewire so that those components of the device in their retracted form have essentially the same cross-sectional profile as the guidewire, itself. The present invention also provides a thin sleeve which holds the filter and self-expanding stent against the guidewire. The thin sleeve is then retracted proximally relative to the guidewire allowing the filter and self-expanding stent (or other expansion means) of the present invention to expand. The same guidewire which is used to place the emboli capture device of the present invention is used to guide the surgical catheter into place for performing the angioplasty or other intravascular surgery. The catheter, itself, is utilized to retract and retrieve the emboli capture device at the conclusion of the procedure.

A primary object of the invention is to provide a low profile emboli capture device.

Another major object of the invention is to provide an emboli capture device capable of use in carotid and saphenous vein graft angioplasty and stenting without occlusion of blood flow.

A further object of the invention is to provide an emboli capture device which, in its retracted position, has a filter and self-expanding stent (or other expansion means) carried in a reduced cross-sectional region of the guidewire so that the filter and self-expanding stent (or other expansion means) combination in its retracted position have a cross-sectional area essentially the same as the cross-sectional area of the guidewire.

A further object of the invention is to provide a low profile emboli capture device carried near the distal end of a standard guidewire and having a thin sleeve holding the expandable stent (or other expansion means) and filter in a retracted position on the guidewire and wherein the sleeve may be moved to a second position allowing the device to expand outwardly and contact the arterial wall.

Yet another object of the invention is to provide an emboli capture device having an outer diameter of approximately 0.020 inch when used with a currently standard guidewire of 0.014 inch and wherein that dimension represents the effective insertion diameter of the device, since insertion of the device may be done without using a catheter.

A further object of the invention is to provide an emboli capture device having a low profile and which is carried at the distal end of a standard diameter guidewire, wherein the same guidewire is utilized to guide a surgical catheter into position for an angioplasty or other intravascular procedure, and wherein the catheter utilized to perform the surgery is also utilized to retract and retrieve the emboli capture device at the conclusion of the surgical procedure.

Other objects and advantages of the invention will become apparent from the following description and the drawings wherein:

BRIEF SUMMARY OF THE DRAWINGS

FIG. 3 illustrates a section of a standard guidewire having a mounting region of reduced cross-sectional area, FIG. 4 is a schematic representation of that portion of the guidewire shown in FIG. 3 wherein the expandable stent and filter components of the present invention are shown schematically in their folded or retracted position within the reduced cross-sectional mounting region of the guidewire;

FIG. 5 is a schematic representation showing the movable sleeve in position over the retracted and folded expandable stent and filter;

FIGS. 29A through D are schematic illustrations of alternate expansion means capable of use in the present invention; and FIG. 30 illustrates an alternate form of the invention wherein the mounting region is a recess formed with only a proximal end wall and wherein the guidewire has a tapered distal end.

DETAILED DESCRIPTION OF THE DRAWINGS

Figure 1:
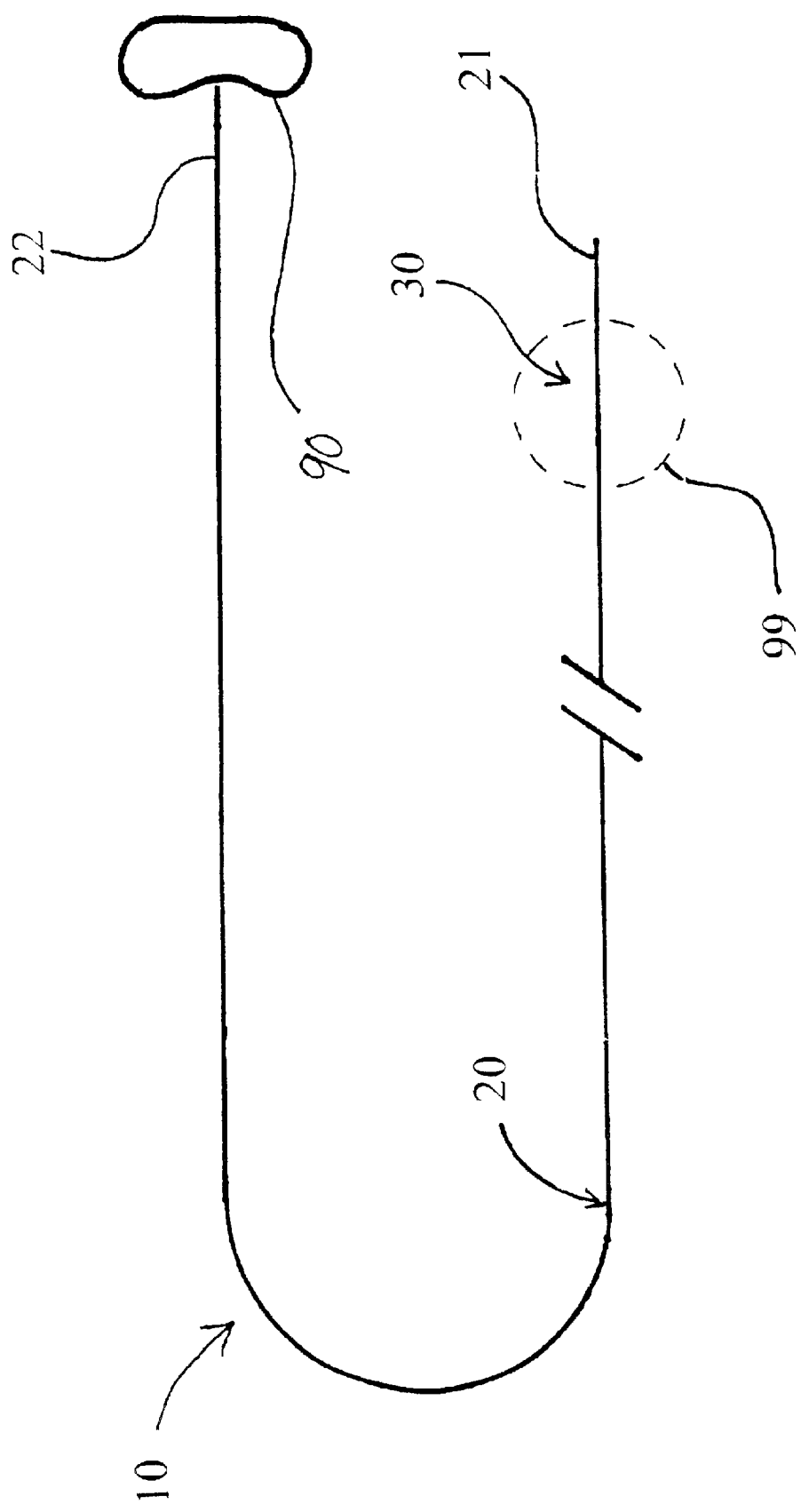
FIG. 1 is a schematic representation of the emboli capture device of the present invention with an expandable stent and filter carried near the distal end of the guidewire in the region circled with a dotted line.

FIG. 1 illustrates the emboli capture device, generally as 10, used in conjunction with a standard guidewire 20 having a distal end 21 and a proximal end 22. The guidewire 20 may be a standard, widely used guidewire presently in use having an outer diameter of approximately 0.014 inch. The emboli capture device includes components within the dotted circle 99 of FIG. 1 that are shown in detail in subsequent drawings.

Near the distal end 21 of guidewire 20 is a mounting region 30 which is shown in greater detail in the other drawings. The circle shown in dotted line 99 of FIG. 1 identifies the area of guidewire 20 which carries the expandable and retractable components of the emboli capture device of the present invention. In practice, the distal end of the guidewire 21 is inserted through an easily accessible artery as is known in the art and the distal end of the guidewire is moved into position downstream or distally of where the angioplasty or other intravascular procedure is to be performed. As is described in greater detail below, the present invention provides a low profile emboli capture device which has an overall outer diameter of approximately 0.020 inch when used with the standard guidewire presently in use having a diameter of 0.014 inch so that it may be utilized in arteries having inner diameters as small as approximately 1 mm. Assuming that future standard guidewires have diameters less than 0.014 inch, the insertion diameter of the present invention would be reduced accordingly.

Figure 2:
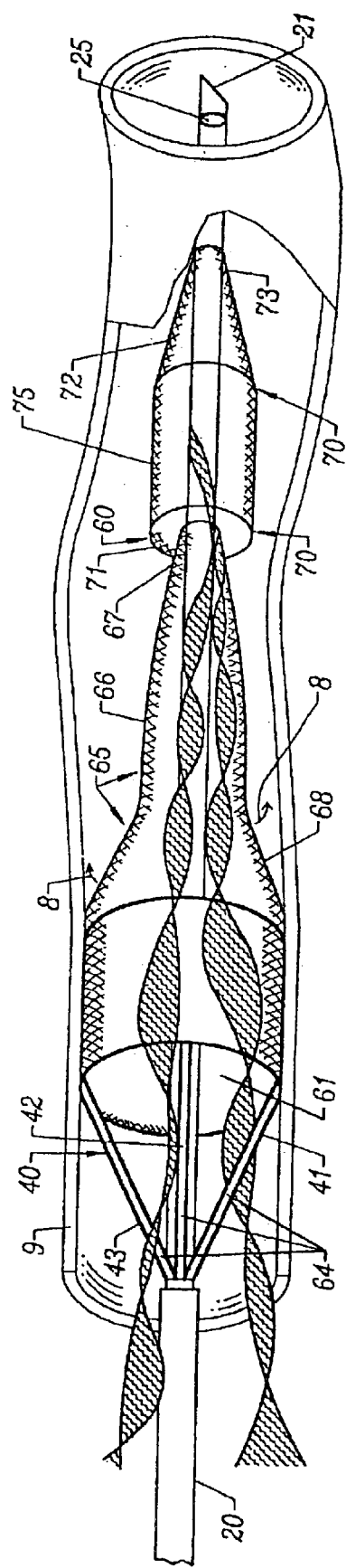
FIG. 2 is a schematic representation partially in section and partially broken away showing the emboli capture device of the present invention in its expanded position inside an artery.

FIG. 2 illustrates a self-expanding stent 40 and filter means 60 in their expanded position wherein the stent 40 has expanded and pushed filter means into a sealing contact with arterial wall 9. The distal end of the guidewire 21 carries a marker 25 to position the stent 40 and filter 60 downstream or distally from that portion of the artery where the angioplasty or other intravascular procedure is being performed.

The stent 40 is the preferred form of expansion means and is preferably a self-expanding stent having a plurality of nitinol arms. The illustrated embodiment has four arms, three of which are visible in FIG. 2 as 41, 42 and 43. The nitinol arms have a shape memory and are formed so that the arms tend to move to their expanded position as illustrated in FIG. 2. A more detailed description of the stent 40 is provided below. The resilient arms 41, 42 and 43 may be compressed against guidewire 20 by exerting an inwardly directed radial force against them compressing them against guidewire 20. As used herein and in the claims, the phrase "expansion means" is used in its broadest sense as any device used to cause filter means 60 to expand. Some alternate "expansion means" are discussed below. The preferred expansion means is a "self-expanding stent," that phrase being used herein and in the claims in its broadest sense as a plurality of arms which have a shape memory expanded position wherein they are capable of contacting arterial walls and supporting a filter such as filter 60 and which may be compressed or folded against the guidewire 20 by radial forces applied against the arms.

Filter means 60 may be of a variety of shapes but the preferred shape is a dual chamber, elongated shape illustrated in FIG. 2. Filter means 60 includes a circular, cylindrical intake 61 of sufficiently large diameter to contact and seal against the arterial wall 9. A plurality of tethers or shrouds 64 connects the intake 61 to guidewire 20. A more detailed description of the tethers is provided below. The intake 61 is connected to a first emboli collection chamber 65. First chamber 65 includes a tapered region 68, and an elongated region 66 having a reduced cross-sectional area at its distal end forming a throat 67. A second emboli collection chamber 70 is connected integrally to first chamber 65 by having an inlet 71 of a larger diameter than the throat section 67 of first chamber 65. The second chamber 70 has a cylindrical region 75 and a tapered region 73 near its distal end 72 and contacts guidewire 20 at its distal end 72.

The purpose of the second emboli collection chamber 70 is to collect the hardest and most dense particles of plaque captured by the filter means 60. The first, upstream chamber 65 is designed to capture the softer pieces of plaque. If the first chamber 65 becomes partially filled with plaque during the surgical procedure, its contents may be suctioned out by the catheter used during the surgical procedure.

The first chamber 65 is designed with a tapered section 68 through which the contained plaque moves toward the smaller cylindrically shaped section chamber 66. The tapered region 68 allows blood in the artery 9 to flow freely therethrough, as shown by arrows 8, and around the reduced section 66 of chamber 65 even if the reduced section 66 is completely filled with emboli. The design of elongated and dual chambered filter means 60 is to provide ample storage volume for emboli that may be dislodged during the surgical procedure while simultaneously allowing a relatively large cross-sectional area of the filter to allow arterial blood to flow through the filter, as shown by arrows 8, even though the filter contains a significant amount of captured emboli in chambers 65 and 70. The secondary chamber 70 and the downstream section 66 of chamber 65 are sized so that, when fully expanded, they occupy less cross-sectional area than the cross-sectional area of artery 9, so that blood flow through artery 9 is not restricted.

Figure 27:
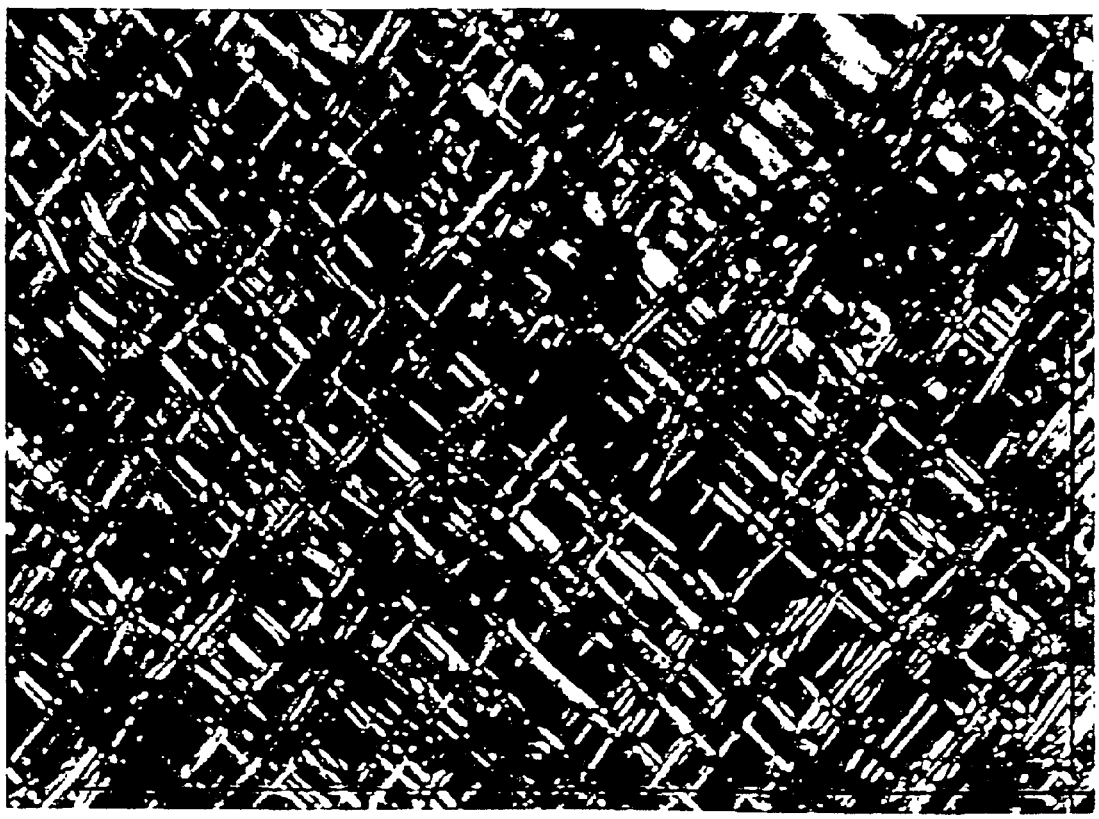
FIG. 27 is a microscopic photograph of the multi-layer mesh filter material used in the preferred embodiment of the invention, shown at 45 times magnification.

Filter means 60 is preferably formed from polymer Corethane in a solvent solution to form a fused, multi-layered and thin walled mesh (i.e., 0.003 inch) having pores or orifices of predetermined size to trap emboli, as small as 20 microns if desired. The preferred pore or orifice size will trap emboli of 50 microns or larger. The filter mesh is produced with a 30 nozzle spinnaret which extrudes Corethane fibers into filaments of about 10 to 30 microns diameter over a mandrel having the shape of the desired filter. The angle of winding the filaments varies from about 30° to 50° relative to the horizontal axis of rotation of the mandrel. The spinnaret reciprocates back and forth between the ends of the mandrel. The preferred filter mesh shown in FIG. 27 has been achieved with 20 passes (one pass including one forward motion and one backward motion of the spinnaret) at 45° and having a resultant wall thickness of 0.0025 inch, and orifices or pores small enough to trap 100 micron and larger emboli or other debris. Suitable filter material may be achieved using between 5 and 50 passes at between a 30° and 55° angle from the horizontal. The multiple layers in the filter mesh fuse together by solvent joining. Evaporation of solvent is caused by IR (infrared) heaters. Background information on spinning vascular grafts is described in U.S. Pat. Nos. 4,475,972 and 5,163,951, both of which are hereby incorporated by reference.

Figure 28:
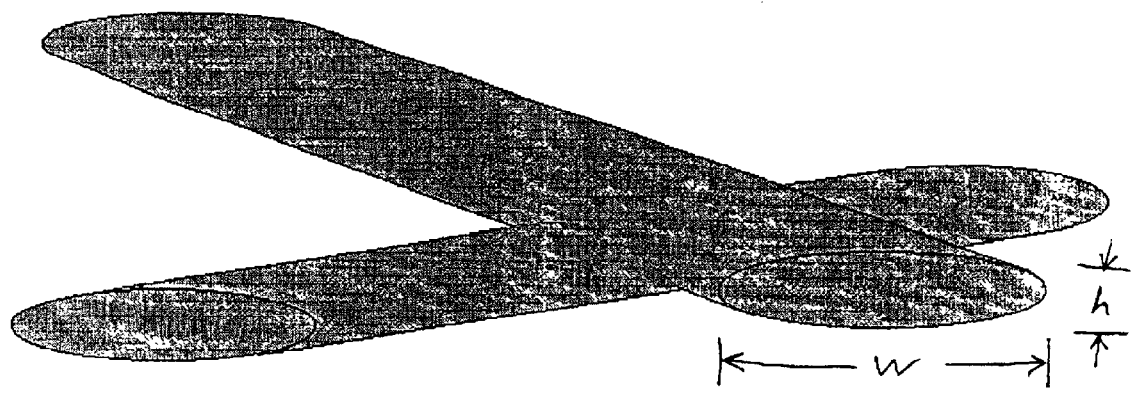
FIG. 28 is a schematic illustration of an alternate multi-layer mesh filter material wherein each filter has been formed with a flattened or slumped cross-section.

A significant alternate embodiment of the filter mesh is shown schematically in FIG. 28, wherein the cross-sectional profile of each filament has been flattened by "fiber slumping" which includes application of heat to the extruded filaments. The resulting "fiber slumped" filaments have cross-sections wherein the width "w" is preferably between 1.5 and 3 times the height "h" of the filament, however the ratio of width to height is not limited to that range. The resultant effect is a multi-layered, fused mesh with reduced wall thickness for a given number of passes. For example, applying "fiber slumping" to the mesh shown in FIG. 27 would reduce the wall thickness from 0.0025 inch to about 0.001 inch.

According to the present invention, the mesh may be coated for several purposes. First, the mesh can be coated with a non-thrombogenic coating such as heparin to prevent new clot formation on the mesh surface. Secondly, a hydrogel coating can be applied to the mesh surface. This coating is intended to swell upon contacting aqueous media such as blood. The swollen gel on the mesh reduces the effective size of the pores or orifices provided by the mesh. That feature in turn reduces the number of layers of filter material to achieve the proper size of the orifice or holes. The use of fewer layers of polyurethane material achieves a thinner mesh, keeping the overall profile of the device to a minimum. A further advantage of the hydrogel coating is that the sticky nature of the coating at the edge of the holes tends to help capture emboli particles.

Figure 3:
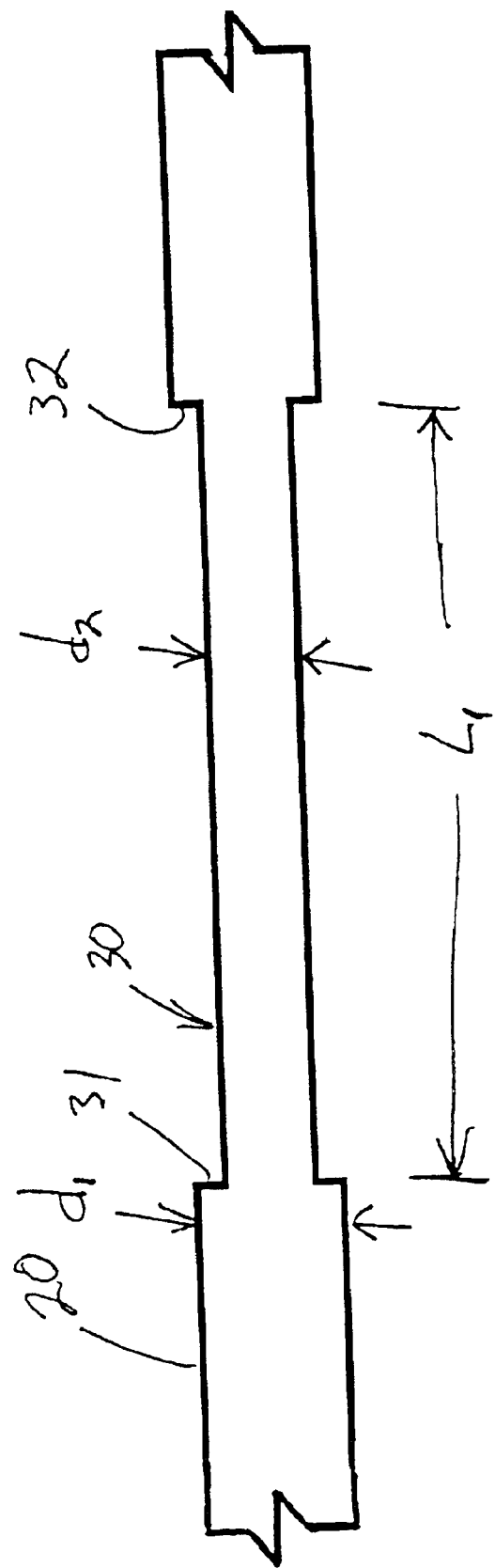
FIGS. 3, 4 and 5 show schematically how the emboli capture device of the present invention is packaged on a standard guidewire and, in particular.
Figure 4:
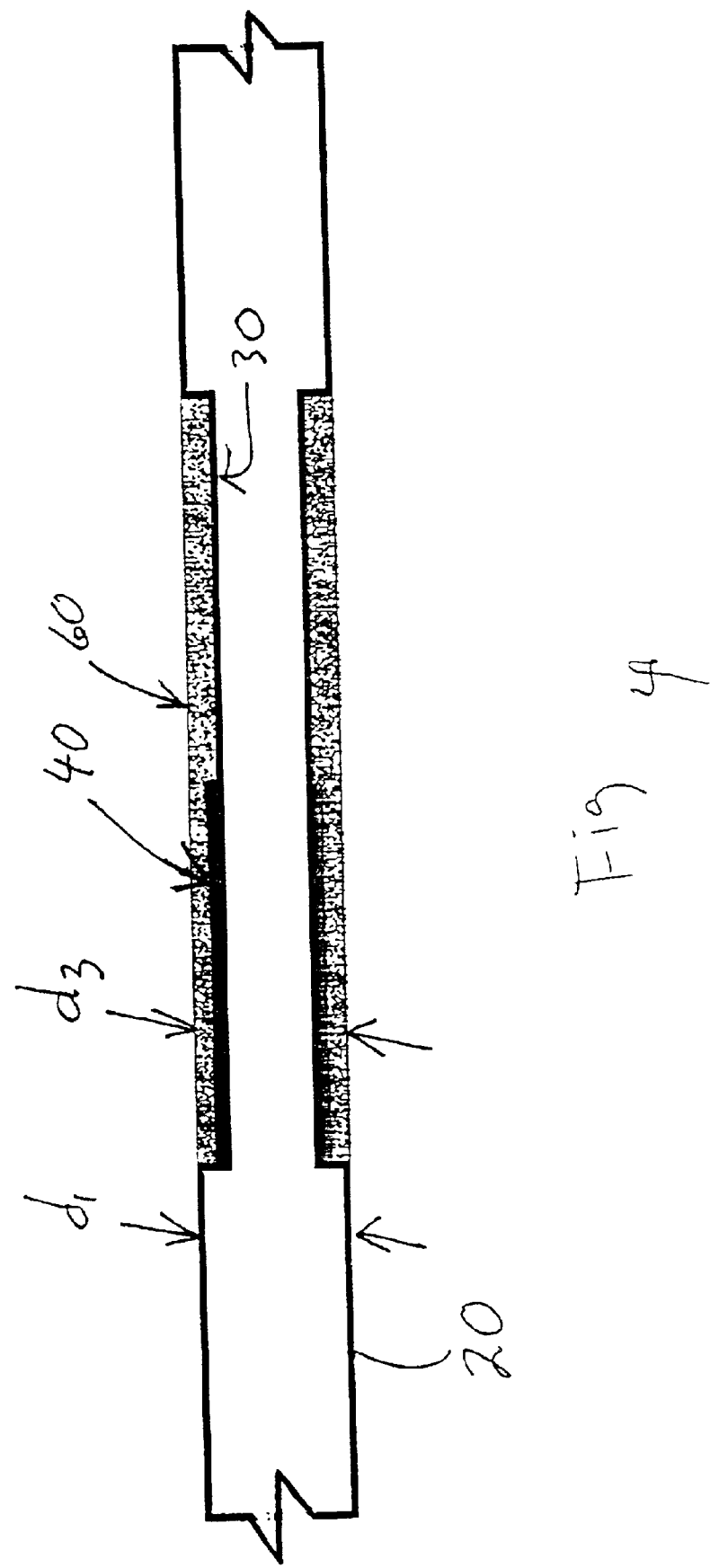
Figure 5:
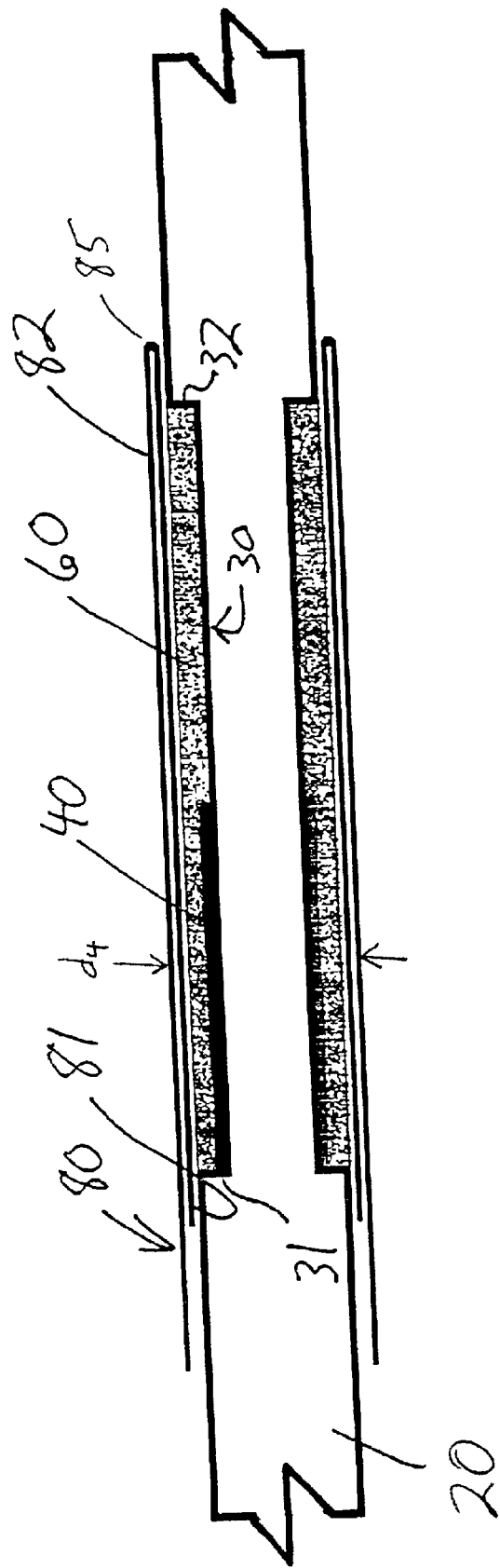

FIGS. 3 through 9 represent schematically how the invention is "packaged" and deployed. These drawings are not to scale and show in exaggerated fashion various aspects of the invention and are presented solely for purposes of illustrating the invention. FIGS. 3–5 show how the self-expanding stent and filter means of the present invention are "packaged" relative to the guidewire 20 to achieve the smallest possible profile. FIGS. 6–9 show how the sleeve is moved to allow the stent/filter combination to expand and deploy.

FIG. 3 shows that portion of the guidewire 20 within the circle 99 of FIG. 1. Guidewire 20 has a stent/filter mounting region 30 which is preferably machined into guidewire 20. In the preferred form of the invention, guidewire 20 has an outer diameter $d_1$ of 0.014 inches and the stent mounting region 30 has an outer diameter $d_2$ of 0.006 inches. In the preferred form of the invention, $L_1$ of mounting region 30 is approximately 17 mm. The length of $L_1$ may vary according to the particular filter and particular stent being used. Mounting region 30 as illustrated in FIG. 3 includes a vertical proximal wall 31 and a vertical distal wall 32. The end walls 31 and 32 of mounting region 30 could be other shapes without departing from the spirit of the invention. The invention alternately could use a tapered guidewire with a reduced cross-sectional region having only a proximal end wall and no distal end wall, as described below.

FIG. 4 shows schematically how the self-expanding stent 40 and filter means 60 are folded against guidewire 20 within mounting region 30. It is significant to note that the overall diameter $d_3$ of the retracted stent 40 and folded filter 60 is approximately the same as the outer diameter $d_1$ of guidewire 20, i.e., 0.014 inches. The phrase "approximately" means that the diameters $d_1$ and $d_3$ are sufficiently close so that the overall performance of the device in being inserted, deployed and retrieved is not compromised. Applicants believe the diameters $d_1$ and $d_3$ should be within 20% of each other. It is to be understood that the self-expanding stent 40 must be compressed and held against the mounting region 30 to be kept in its retracted position illustrated in FIG. 4.

FIG. 5 illustrates how the retracted stent 40 and folded filter means 60 are held against the mounting region 30 of guidewire 20. A sleeve means 80 is provided having an inner first layer 81 that extends over mounting region 30 from a position proximal of end wall 31 to a position distally of end wall 32. Sleeve means 80 has a second outer layer 82 that extends over the first layer 81 from a position 85 where the sleeve is infolded; the infolding is located distally of distal wall 32 of mounting region 30 to a position proximally of proximal end wall 31 of mounting region 30. The double wall sleeve means 80 allows for movement of the sleeve means 80 from its first position illustrated in FIG. 5 to its second position illustrated in FIG. 8 where it no longer holds the self-expanding stent and the self-expanding stent 40 and filter means 60 are free to expand. The double layered sleeve means 80 allows for movement of the sleeve means to its second position without requiring frictional motion of the sleeve means 80 against the folded filter material of filter means 60. As shown in FIG. 5, the overall outer diameter $d_4$ of the assembled device is 0.020 inch, assuming sleeve layers 81 and 82 are each 0.003 inch thickness. The outer diameter $d_4$ shown in FIG. 5 is the "effective insertion diameter" of the device, since it is inserted and deployed without a catheter. It is also within the scope of this invention to utilize a sleeve means 80 having only a single layer extending across mounting region 30. The disadvantage of that embodiment of the invention is the frictional motion of the sleeve means 80 against the material of filter means 60 as the sleeve is moved to a position where the stent 40 is free to expand. Such frictional motion against the filter 60 could possibly adversely affect the opening and performance of filter means 60.

Figure 6:
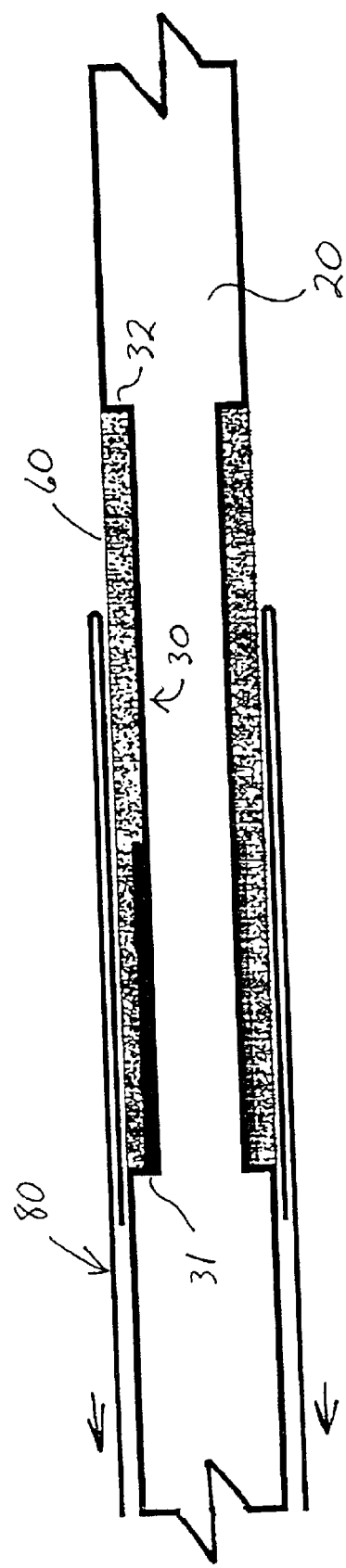
FIG. 6 is a schematic illustration showing the sleeve as it is being moved proximally relative to the guidewire and the retracted stent/filter combination.
Figure 7:
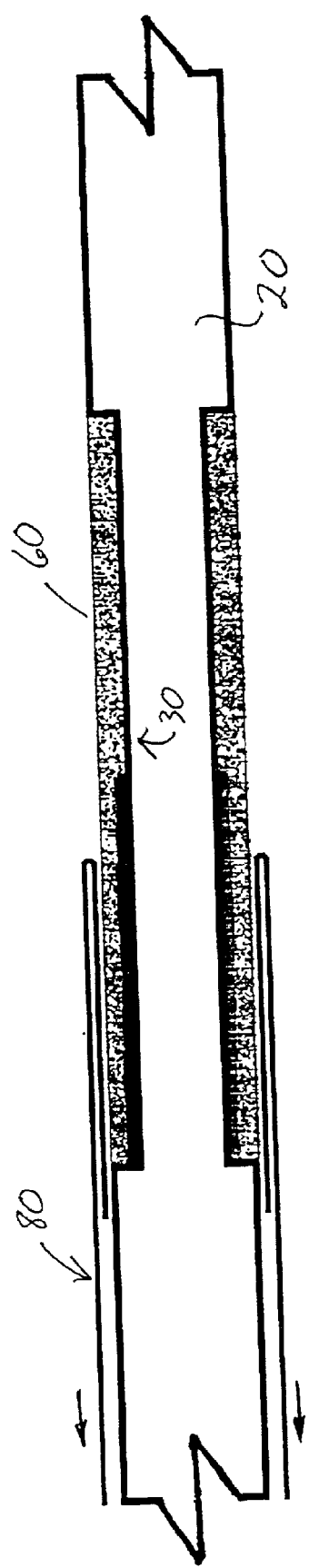
FIG. 7 shows the sleeve of FIG. 6 as it is moved further in the proximal direction relative to the guidewire and the folded stent/filter.
Figure 8:
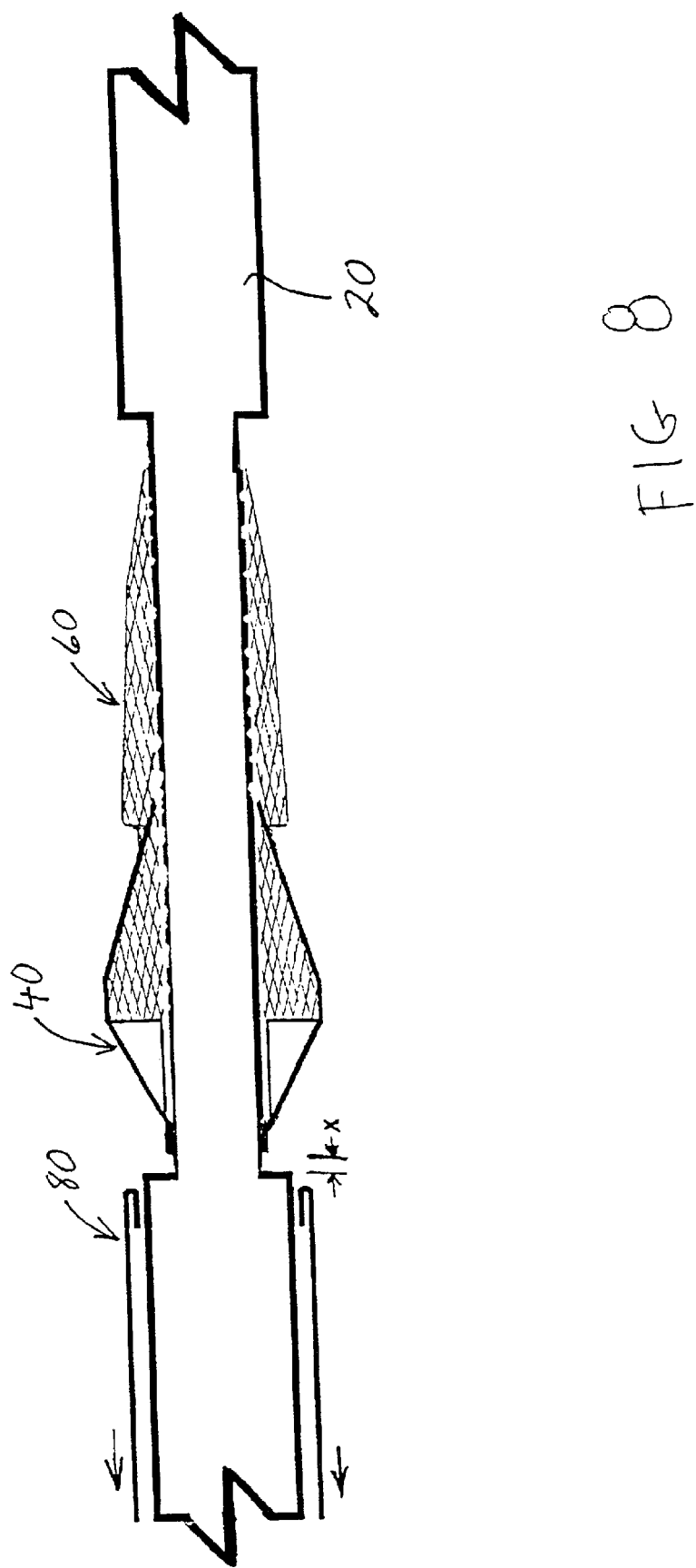
FIG. 8 illustrates the sleeve moved completely off the retracted stent/filter and wherein the stent/filter combination is beginning to expand.
Figure 9:
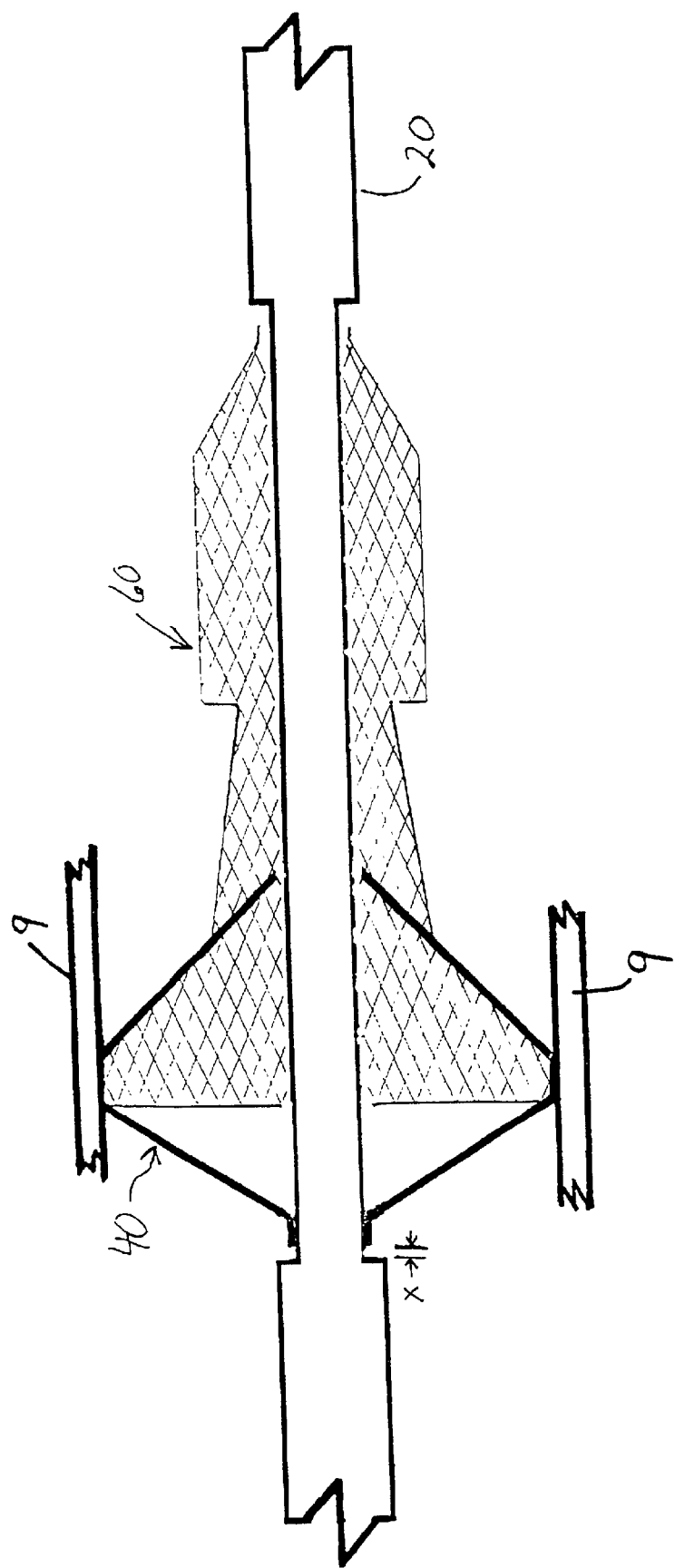
FIG. 9 is a schematic representation showing the emboli capture device in its fully expanded position.

FIG. 6 illustrates that the second layer of sleeve means 80 has been pulled in a direction proximally relative to mounting region 30. FIG. 7 illustrates schematically that the sleeve means 80 has been moved slightly more than half way across mounting region 30. FIG. 8 shows sleeve means 80 moved to a position where it no longer covers any of mounting region 30 and the self-expanding stent 40 and filter means 60 are beginning to expand. FIG. 9 illustrates schematically that the stent 40 and filter means 60 have expanded fully and the intake of the filter means 60 has contacted the arterial wall.

Sleeve means 80 extends lengthwise along guidewire 20 from its double infolded distal end 85 to the proximal end 22 of guidewire 20. A handle 90 (FIG. 1) is carried at the proximal end 22 of guidewire 20, and is bonded to the proximal end of sleeve 80. After the self-expanding stent 40 and filter 60 are deployed in an artery, handle 90 is used (as described below) to remove the sleeve 80 from guidewire 20. FIG. 9 also illustrates that sleeve means 80 has been removed and guidewire 20 is now free to support and guide a catheter (not shown) into place in the artery.

It is significant to note that the use of sleeve means 80 in compressing the stent 40 and filter 60 in mounting region 30, as shown in FIG. 5, maintains the structural stability and "pushability" of guidewire 20. Ordinarily, a guidewire that has a recess formed in it similar to mounting region 30 but, without any material packaged in the recess, would lose much of its columnar compressive strength, or pushability, and become much more likely to bend at one of the end walls 31 or 32.

Figure 10:
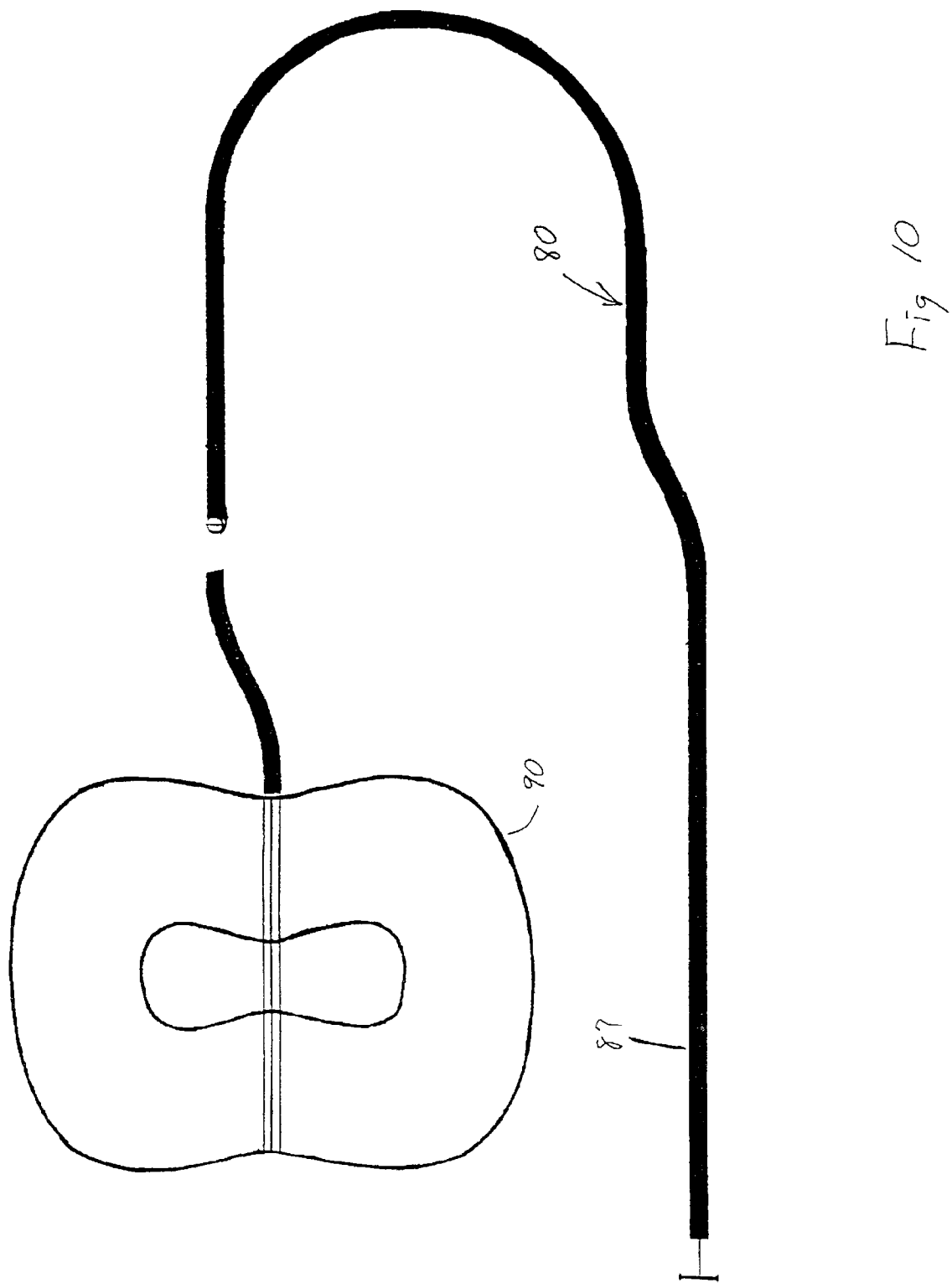
FIG. 10 is a schematic representation showing a sleeve having a cylindrical imperforated shape connected to a handle for moving the sleeve relative to the guidewire.
Figure 11:
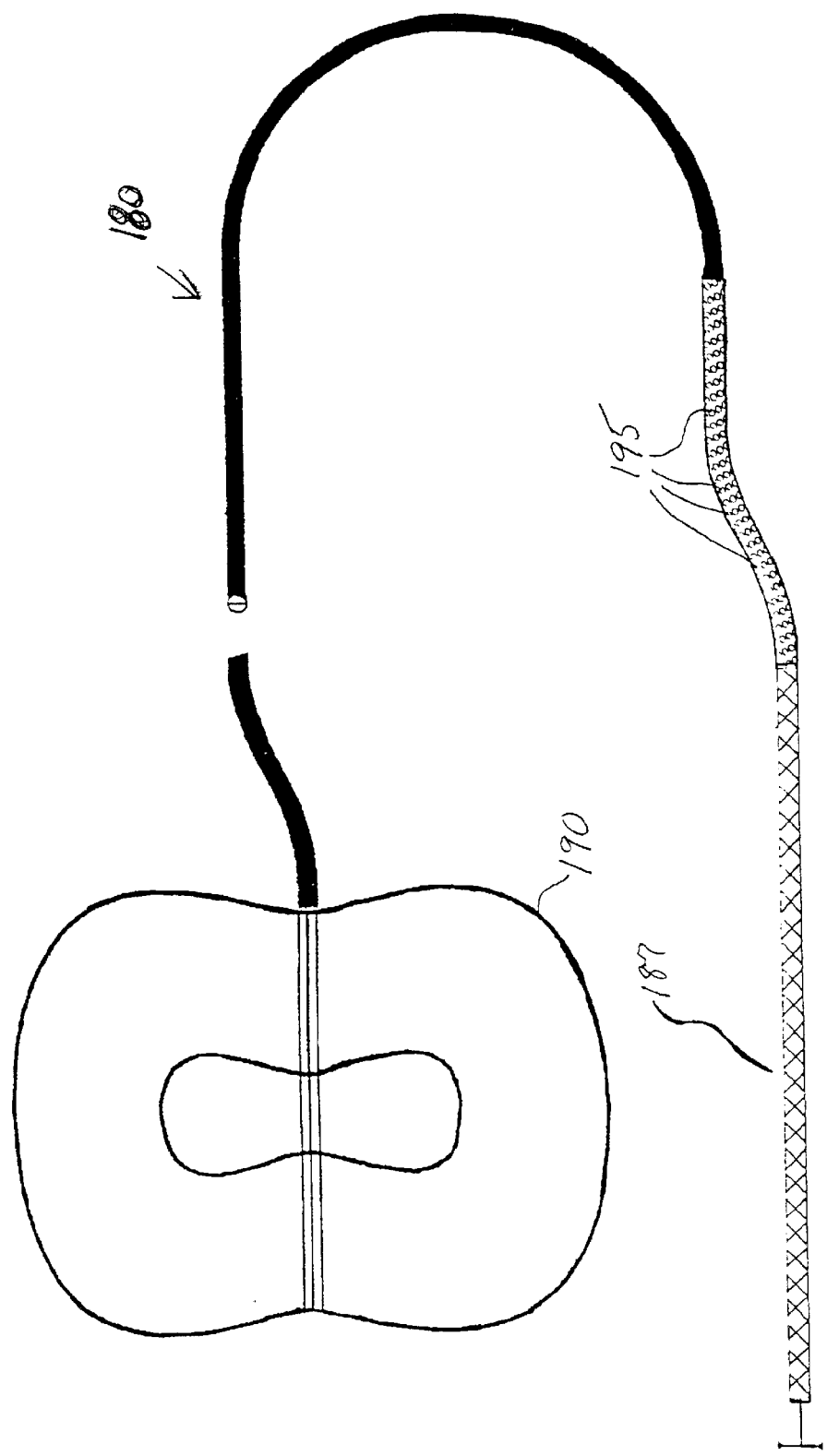
FIG. 11 is a schematic representation of an alternate sleeve having an open woven distal portion and having a plurality of orifices formed in a region near its distal portion for introducing lubricants or medicine.

As shown in FIG. 10, sleeve means 80 may be a solid, imperforate sleeve with a distal end 87. Alternately, as shown in FIG. 11, a second embodiment sleeve 180 has a woven, distal end section 187 that covers the mounting region 30 of guidewire 20. Sleeve 180 is shown in FIG. 11 with a plurality of orifices 195 formed near its distal end section 187. Orifices 195 may be used to introduce lubricant or medicine into the artery to facilitate insertion of the device or placement of medicine within the artery.

Figure 12:
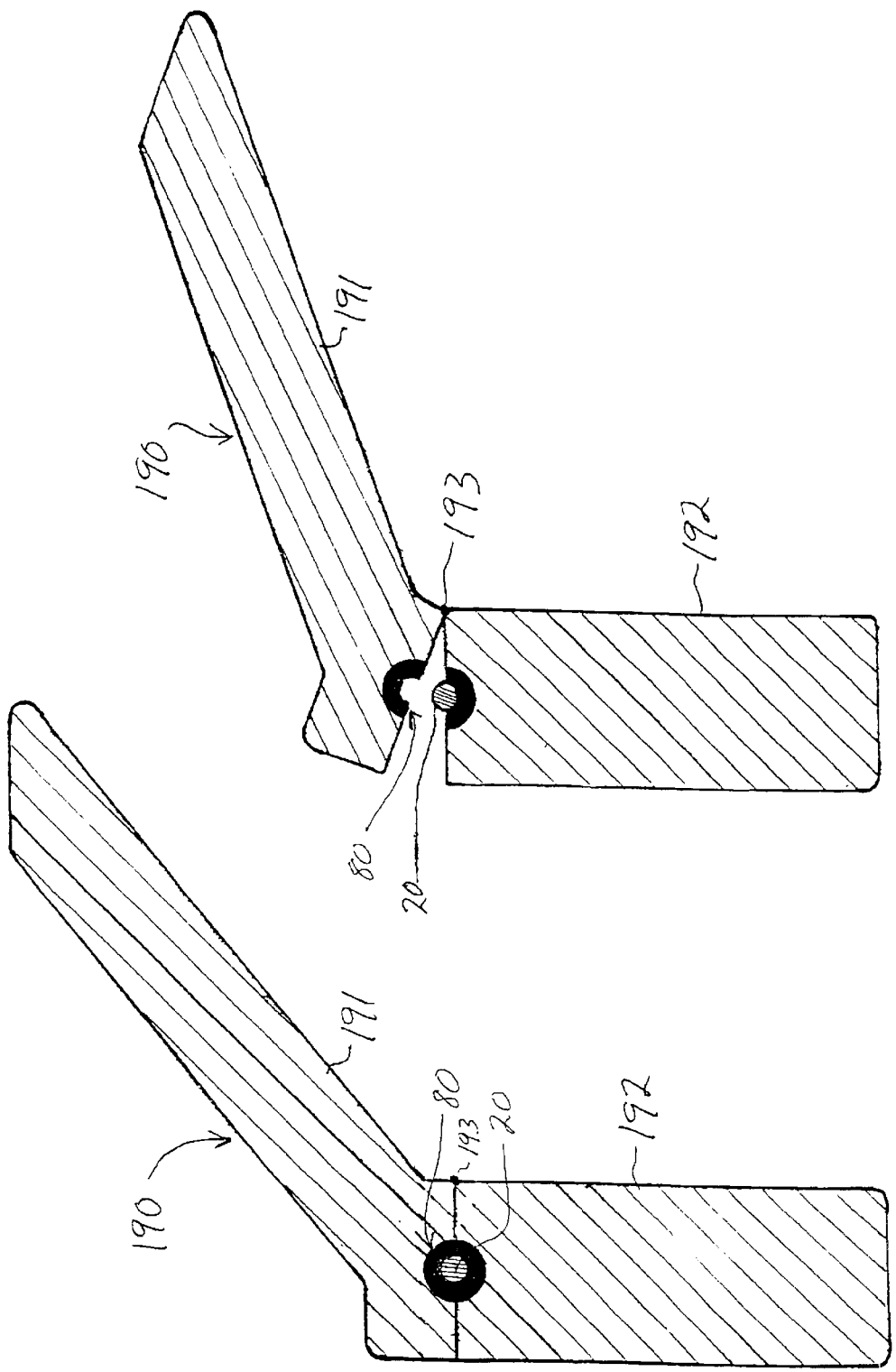
FIGS. 12A and 12B are cross-sectional views of a handle which may be used in the present invention to move the sleeve relative to the guidewire as well as to split the sleeve to allow rapid separation of the sleeve from the guidewire.

Another aspect of sleeve means 80 is that, in its preferred form, it is "splittable" to allow a rapid removal of the sleeve 80 from guidewire 20. Ordinarily, sleeve means 80 would have to be slid completely off the proximal end of guidewire 20. As shown in FIG. 12, the sleeve means 80 is bonded to handle 190 and may be split by simply opening handle 190. Openable handle 190 has two parts 191 and 192 that are pivotally connected at hinge 193. Sleeve means 80 is bonded to the two parts 191 and 192. Opening the handle splits sleeve means 80 so that it may be easily separated from guidewire 20. Sleeve means 80 has a longitudinally extending line of weakening, so that as it is withdrawn from the patient's body, it is simply split away from guidewire 20 rather than having to be slid off the proximal end of guidewire 20. This splittable sleeve feature allows the use of a shorter guidewire, decreases the time required to perform the procedure, and in many cases, requires one less person in the operating room to perform the procedure.

Figure 13:
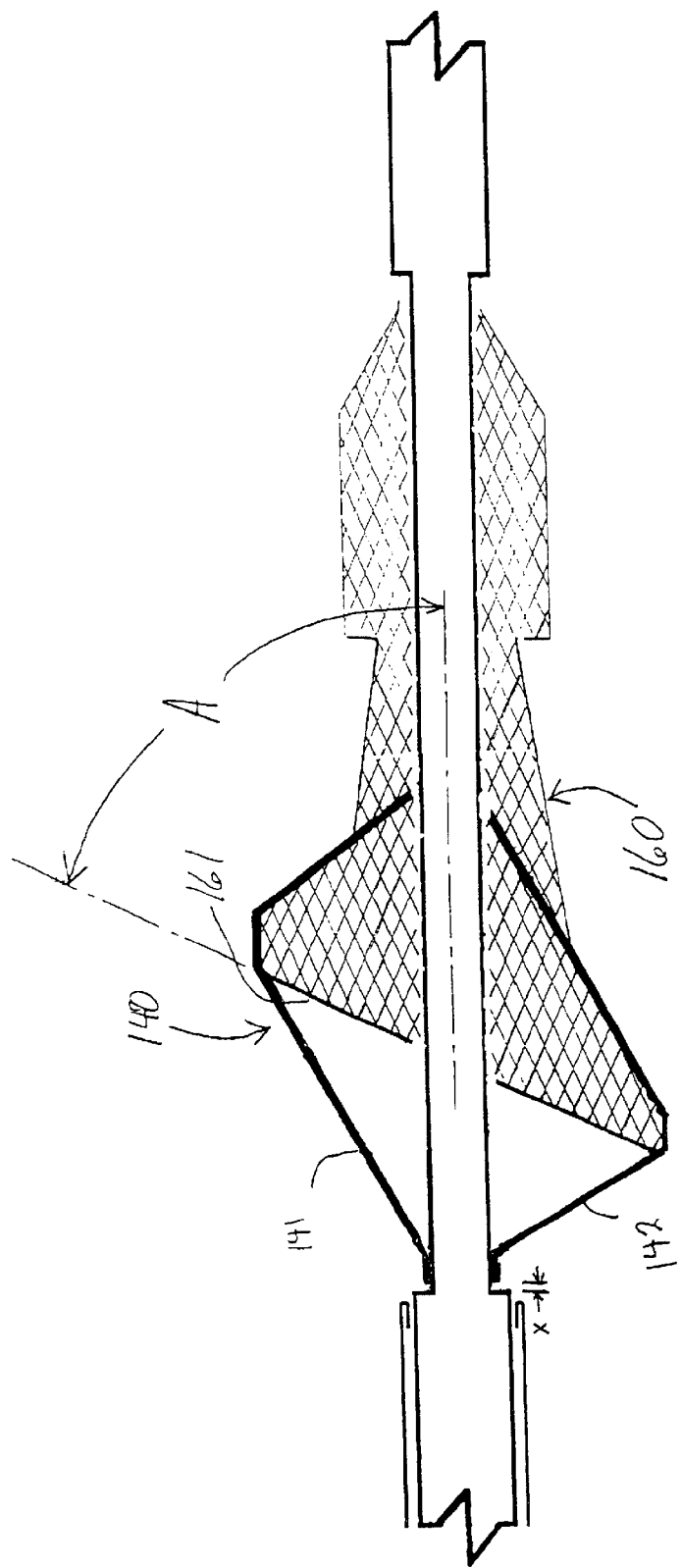
FIG. 13 is a side elevational view, partially in section, showing an alternate form of the invention having an elliptical opening formed in the filter and in the stent used to deploy the filter.
Figure 14:
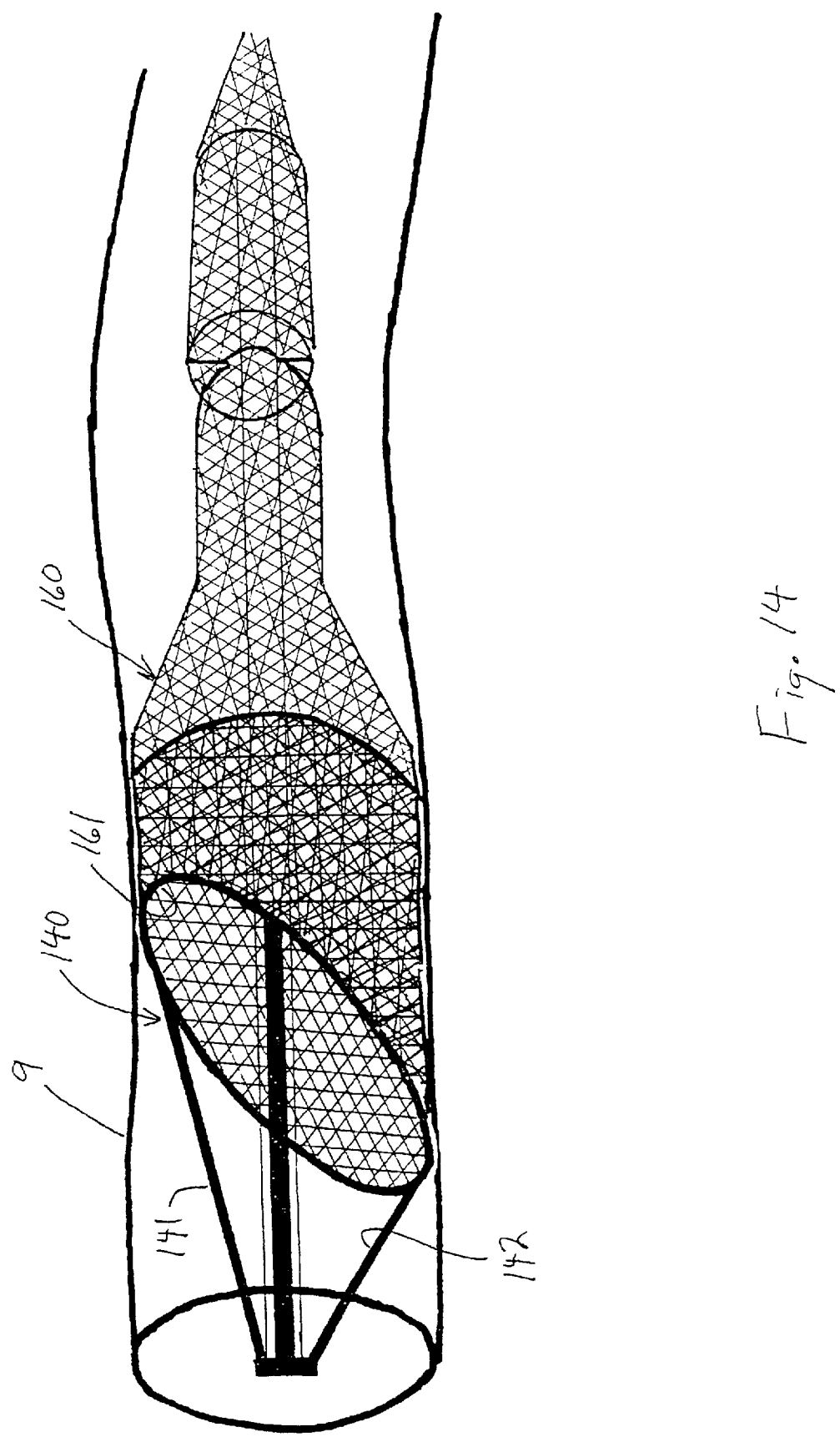
FIG. 14 is a side elevational view of the stent and filter combination of FIG. 13 having an elliptical opening and showing the elliptical opening in contact with the arterial wall.

Another significant variation of the present invention is the use of an alternate self-expanding stent 140 and filter means 160 to achieve an angular placement in the artery as shown in FIGS. 13 and 14. The purpose of this design is to achieve a more complete seal of the filter means 160 against the walls of the artery. The angular orientation is achieved by providing stent 140 with arms 141,142 of different lengths and filter means 160 with an elliptical opening 161. The angular orientation A between the longitudinal axis of the guidewire 20 and the filter inlet 161 is between 30° and 90°. In all other significant respects, the device is the same as the first embodiment shown in FIGS. 2–9.

Figure 15:
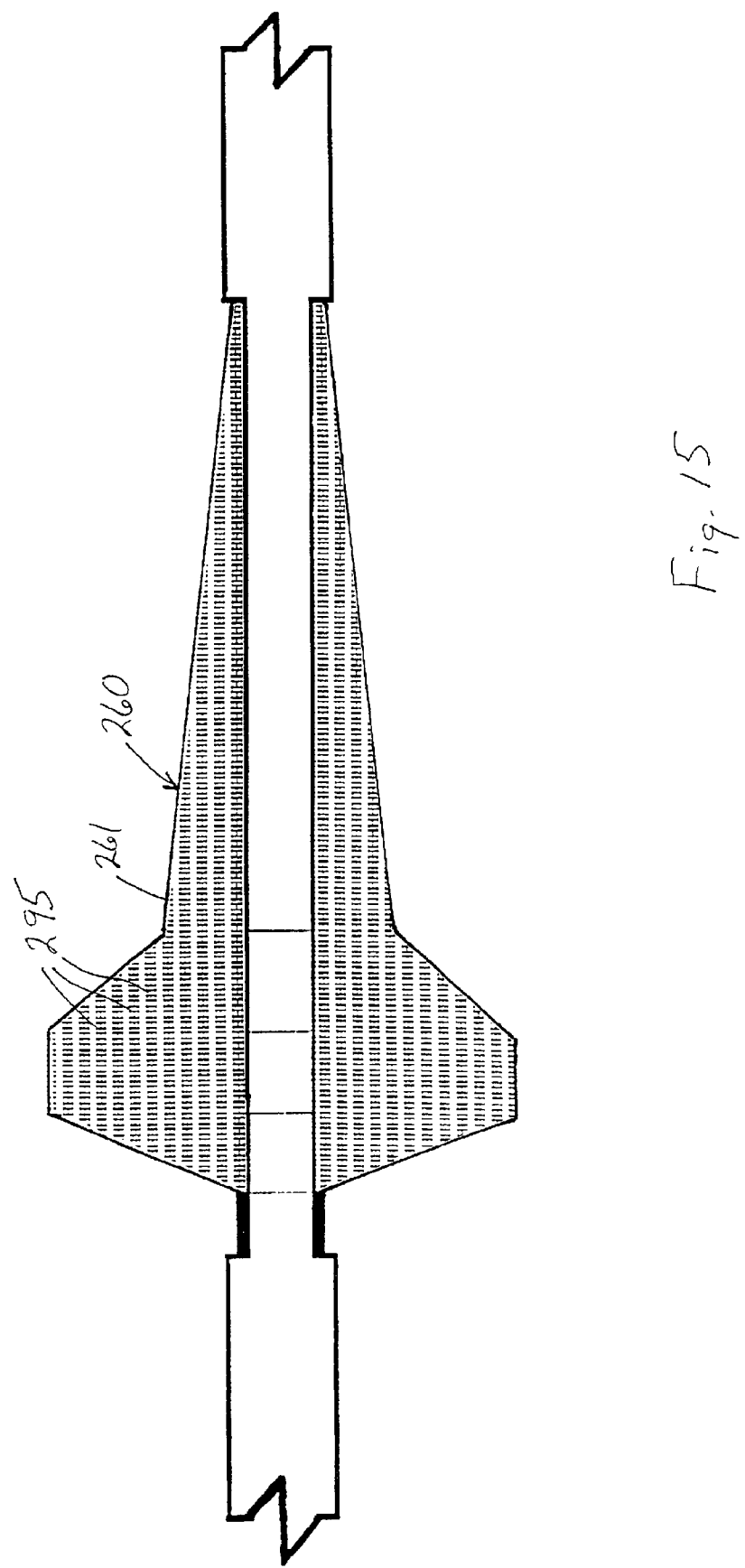
FIG. 15 is a schematic representation of an alternate filter used in the invention wherein the filter is a plastic material with generally H-shaped perforations formed by laser cutting.
Figure 16:
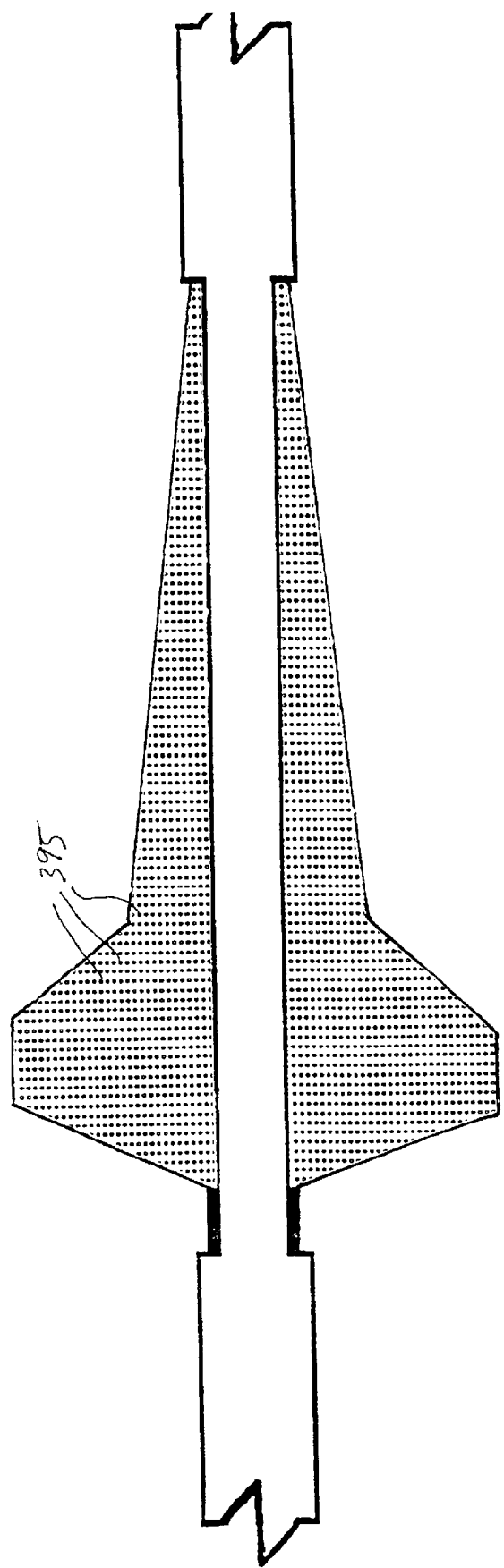
FIG. 16 is a schematic representation of an alternate filter used in the invention wherein the filter is a plastic material with circular shaped perforations formed by laser cutting.

Another embodiment of the invention utilizes a filter means 260 (FIG. 15) which is a plastic tube 261 wherein a plurality of laser cut perforations 295 is formed. As shown in FIG. 15, each perforation is generally H-shaped. Alternately, as shown in FIG. 16, the perforations 395 could be circular with sufficiently small diameters to allow blood to pass through, but not emboli.

Figure 17A:
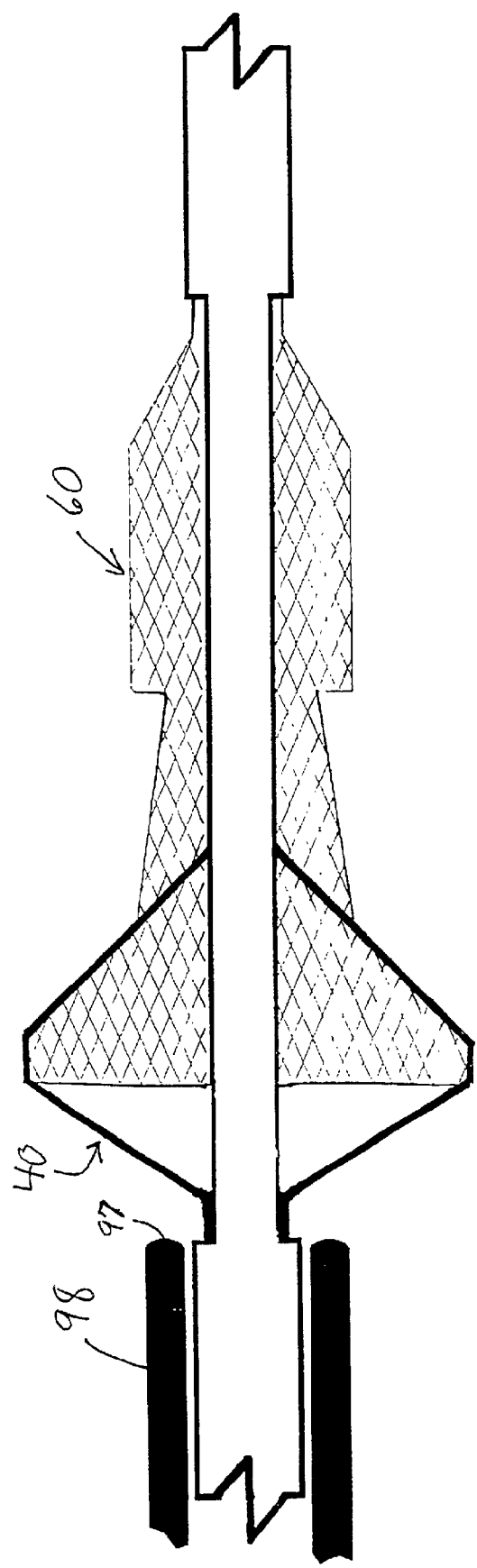
FIGS. 17A through D are schematic representations showing how the emboli capture device shown in FIG. 2 is retracted and retrieved at the end of the angioplasty or other intravascular procedure by using a catheter.
Figure 17B:
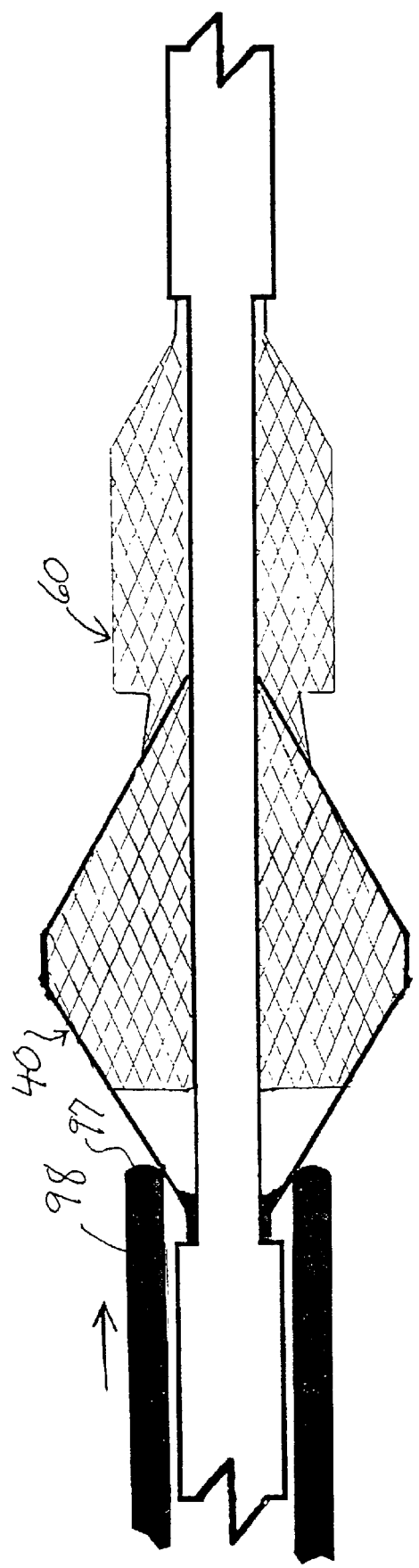
Figure 17C:
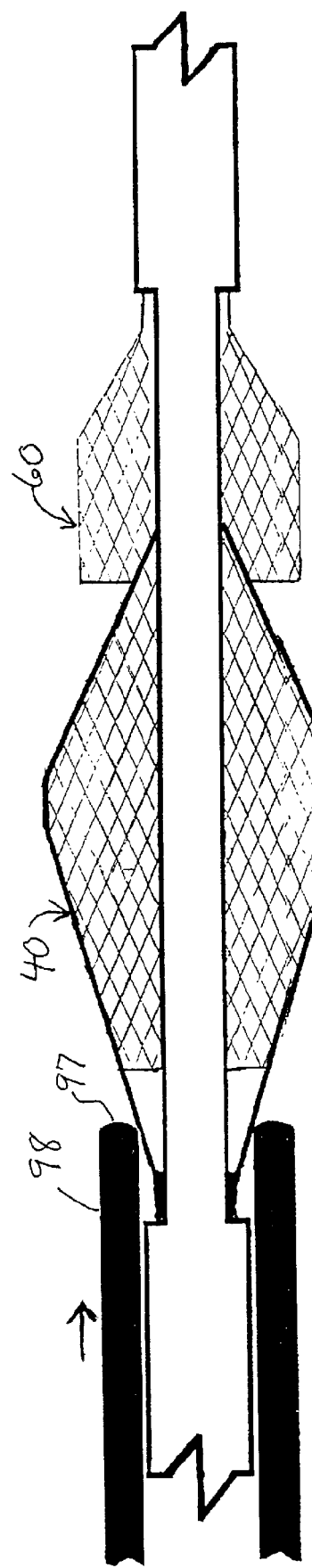
Figure 17D:
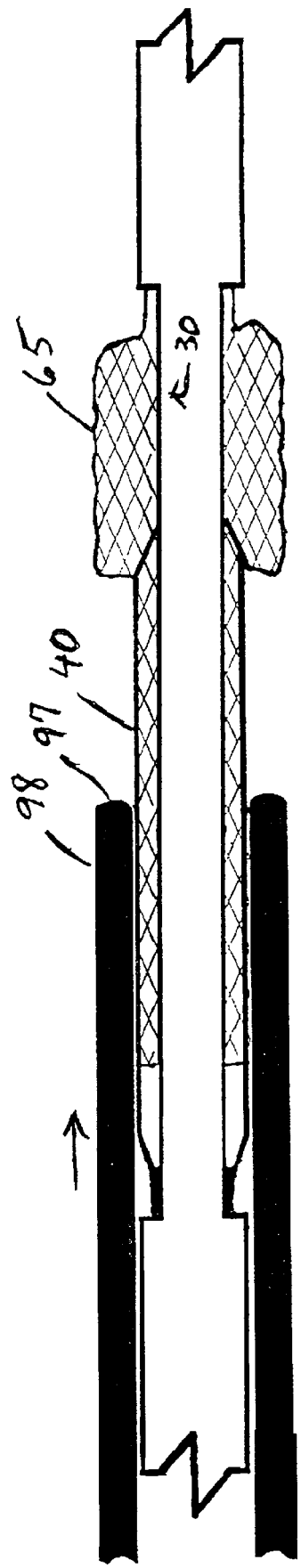
Figure 18A:
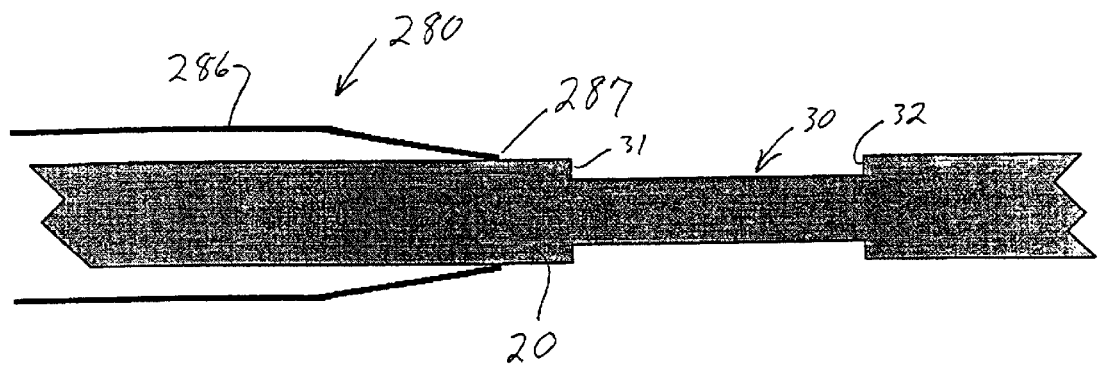
FIGS. 18A and 18B are schematic representations showing the application of a third form of sleeve.
Figure 18B:
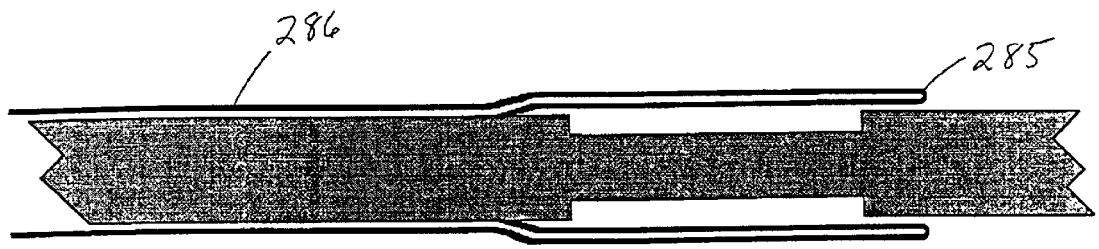

FIGS. 17A through D show how the catheter 98 utilized to perform the angioplasty or other intravascular procedure is used to retract and retrieve the deployed or expanded stent 40 and filter 60. The catheter is moved distally as shown in FIGS. 17A and 17B and begins to collapse the stent 40 and filter 60. FIG. 17C shows a further collapse or retraction of stent 40 and filter 60. Filter 17D shows the catheter advanced to a position where the stent 40 is fully collapsed and the extreme distal end 97 of the catheter 98 is approximately at the midpoint of the mounting region 30. The second chamber 65 will contain emboli and the outer diameter of chamber 65 with emboli will typically be approximately the same or less than the outer diameter of catheter 98. Once the catheter has reached the position shown in FIG. 17D, where the stent 40 is fully collapsed and retracted against guidewire 20, the catheter and guidewire are slid as a unit outwardly from the artery and out of the patient's body.

FIGS. 18–21 illustrate alternate embodiments of sleeve means 80 and particularly the manner in which sleeve means 80 is applied to the guidewire. FIGS. 18A and B illustrate a third embodiment of sleeve means 280 and illustrate how it is applied over the guidewire 20. FIG. 18A illustrates that the distal end 287 of sleeve means 280 has been crumpled in order to make it significantly more flexible and of slightly smaller diameter than the main body 286 of sleeve 280. The clearance between the sleeve body 286 and guidewire 20 is exaggerated for illustrative purposes. The extreme distal end 281 is threaded over guidewire 20 and is held in place proximally of mounting region 30 on guidewire 20 by either an adhesive bond 289 (or by frictional engagement) with the surface of guidewire 20. FIG. 18B shows that, as sleeve means 280 is moved distally, the larger and non-crumpled portion of the sleeve extends to the distal end of mounting region 30. In this position, the sleeve has an infolding 285 distally of mounting region 30 and is ready to be moved in the proximal direction to release the stent/filter assembly (not shown for clarity).

Figure 19:
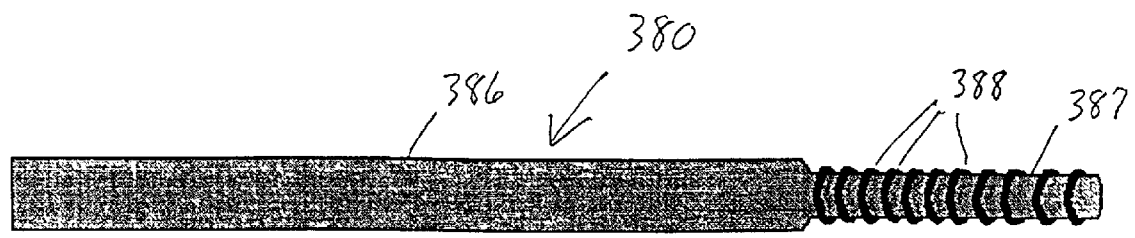
FIG. 19 is a schematic representation showing the application of a fourth form of sleeve onto the guidewire.
Figure 20:
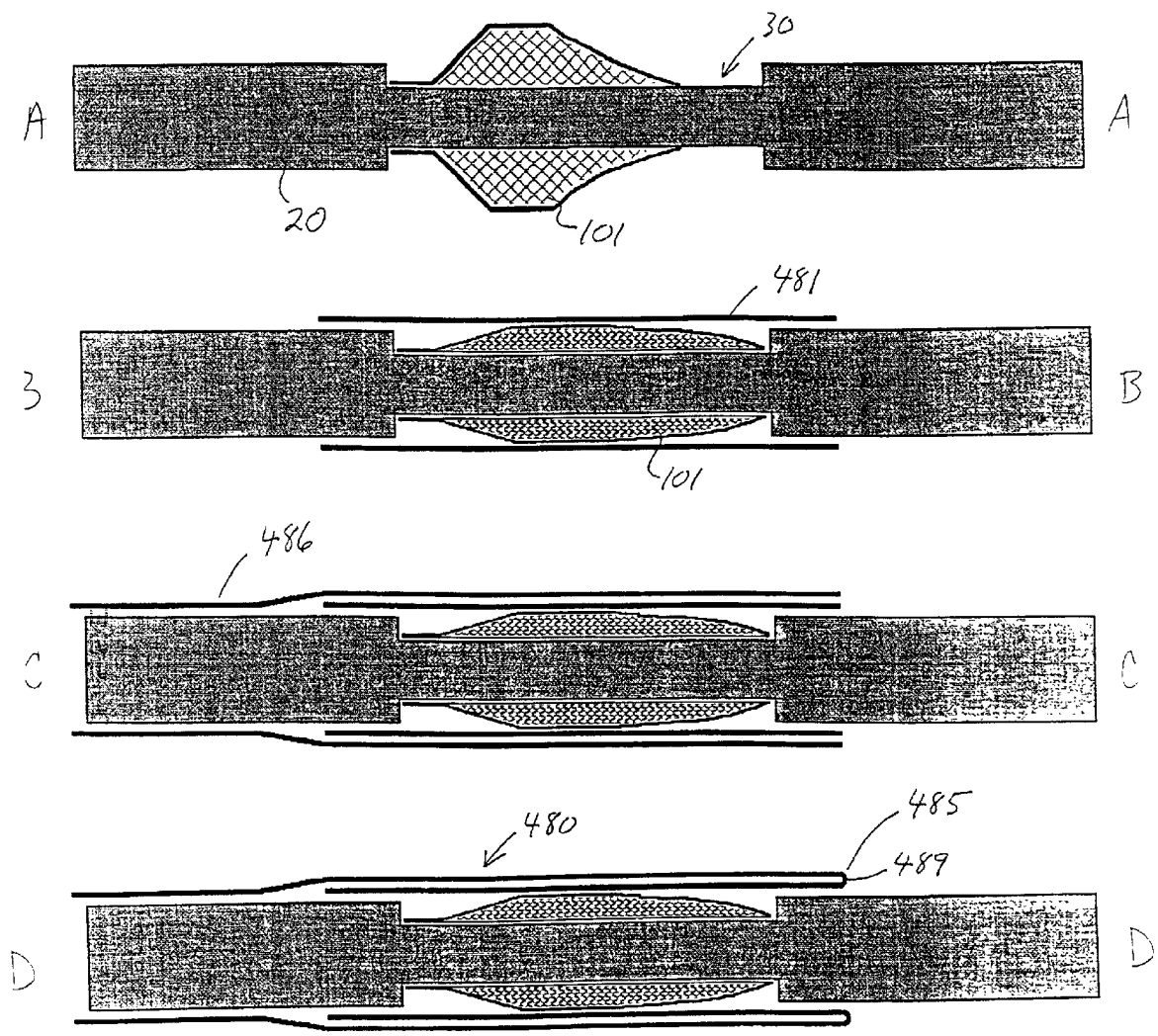
FIGS. 20A through D are schematic representations of a fifth form of sleeve means and how it is applied over the guidewire and the stent/filter assembly.
Figure 21:
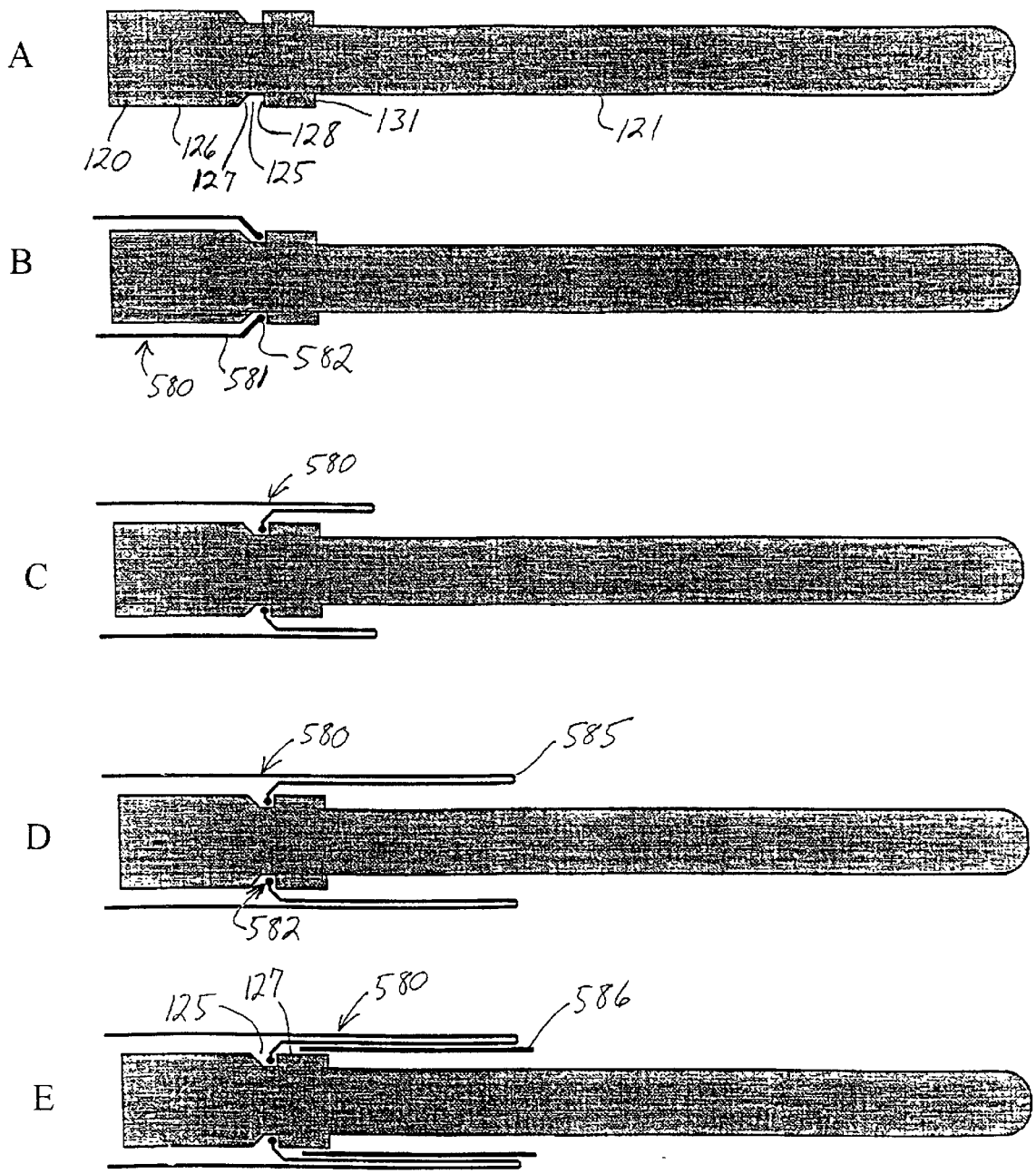
FIGS. 21A through I are schematic illustrations showing a sixth form of the sleeve and how it is applied to a modified guidewire, and illustrating how the stent/filter assembly may be installed from the distal end of the guidewire.
Figure 21:
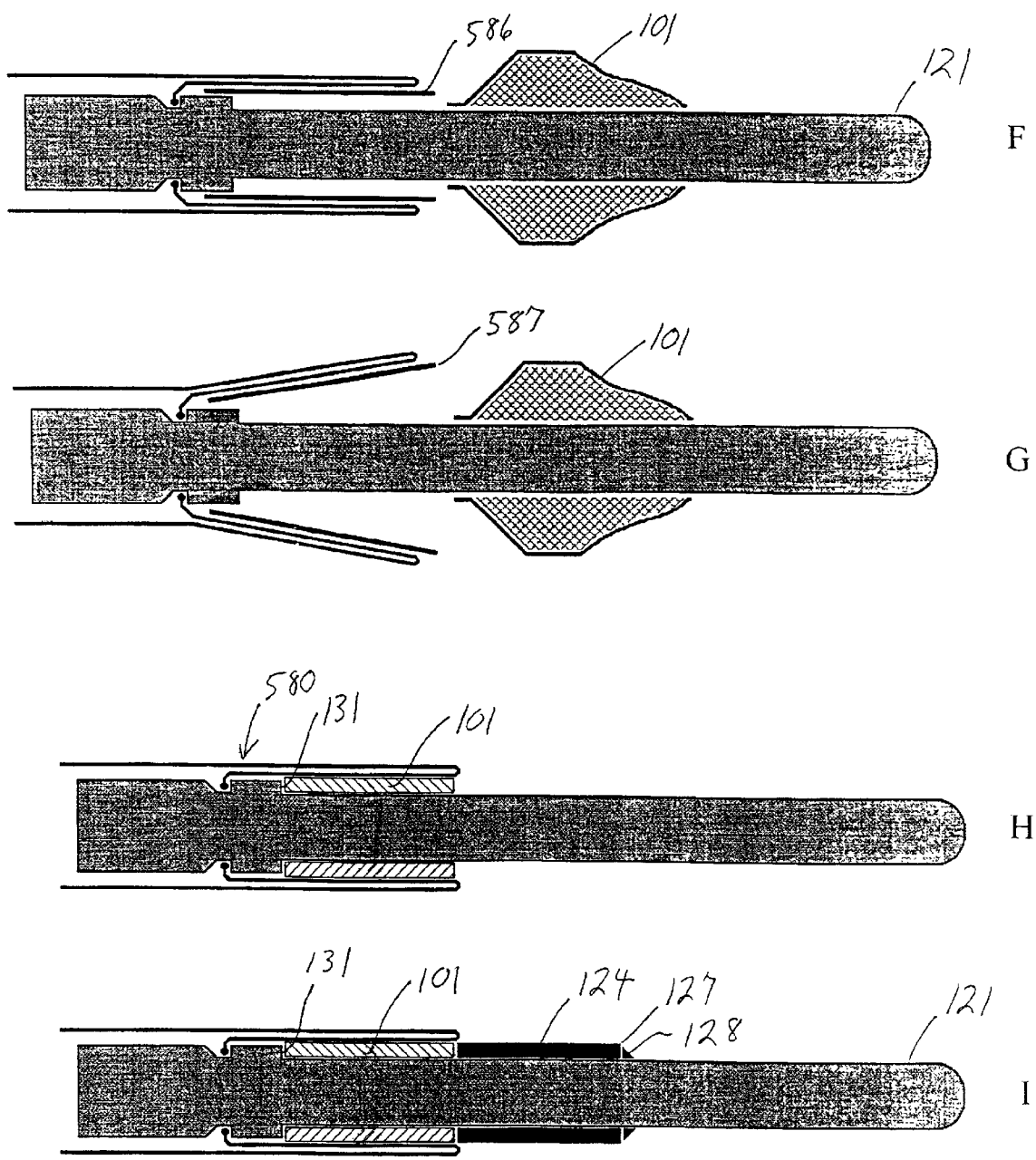

FIG. 19 illustrates a fourth embodiment of sleeve means 380 having body 386, wherein the distal end 387 carries a helical spring 388 to compress distal end 387 and the stent/filter assembly against guidewire 20. The embodiment shown in FIG. 19 is not preferred, because of the friction between sleeve 380 and the stent/filter assembly as sleeve 380 is removed proximally.

FIGS. 20A through D illustrate a fifth type of sleeve means 480 and its manner of application to the guidewire 20 and over the stent/filter assembly 101. FIG. 20A illustrates the stent/filter assembly 101 in position on mounting region 30. FIG. 20B illustrates the placement of a first layer 481 of sleeve material that is drawn into position over mounting region 30 and which compresses the stent/filter assembly 101. FIG. 20C illustrates that the main body portion 486 of sleeve means 480 is drawn over the length of the guidewire 20 and across mounting region 30. The distal ends of first section 481 and of body section 486 are joined by adhesive 489. The sleeve means 480 is now in position with the double fold 485 at its distal end as described above.

FIGS. 21A through I illustrate another sleeve means 580 and the manner in which it is applied to an alternate guidewire 120. As shown in FIG. 21A, alternate guidewire 120 has its entire distal end 121 formed with a reduced diameter of, for example, 0.008 inches while the main body 126 of guidewire has a diameter of 0.014 inch. The design of the distal end 121 of guidewire 120, illustrated in FIG. 21A, allows the loading of the stent filter assembly 101 over the distal end 121 of guidewire 120. A sleeve retaining groove 125 is formed in the surface of guidewire 120 near the proximal wall 131 of mounting region 130. The retaining groove 125 has a gently sloping proximal surface 127 and a distal end wall 128, which is generally perpendicular to the surface of guidewire 120. As illustrated in FIG. 21B, the distal end 581 of sleeve means 580 carries a spring loaded collar 582 which is intended to seat in the sleeve retaining groove 125. As shown in FIGS. 21C and D, the sleeve means 580 is moved distally with respect to guidewire 120, to achieve the double fold 585 discussed above, with spring loaded collar 582 anchored in the sleeve retaining groove 125.

As shown best in FIG. 21E, a sleeve spreader 586 is inserted from the distal end of guidewire 120 and is slid underneath the distal end of sleeve means 580 and contacts the surface 127 of guidewire 120 adjacent the sleeve retaining groove 125. The sleeve spreader 586 is a generally cylindrical, multi-sectional removable tool that is utilized to spread the distal end of sleeve means 580 and facilitate the insertion of the stent/filter assembly 101 over the distal end 121 of guidewire 120. As shown in FIG. 21G, the sleeve spreader 586 has its distal end 587 expanded to stretch the distal end of sleeve means 580 and to allow the stent/filter assembly 101 to be slid underneath distal end 587. The stent/filter assembly 101 is moved proximally relative to guidewire 120 until it seats against wall 131 or until it is the proper clearance from wall 131, wherein the stent/filter assembly is compressed. The sleeve spreader is then removed distally and the sleeve means 580 compresses the stent/filter assembly against the guidewire 120 as shown in FIG. 21H. As illustrated best in FIG. 21I, a cylindrical ring 124 having an outer diameter of 0.014 inch or less is slid onto the distal end 121 of guidewire 120. The distal end of ring 127 is then welded or otherwise permanently attached to guidewire 120 as shown at 128 and the assembly is ready for use.

Figure 22:
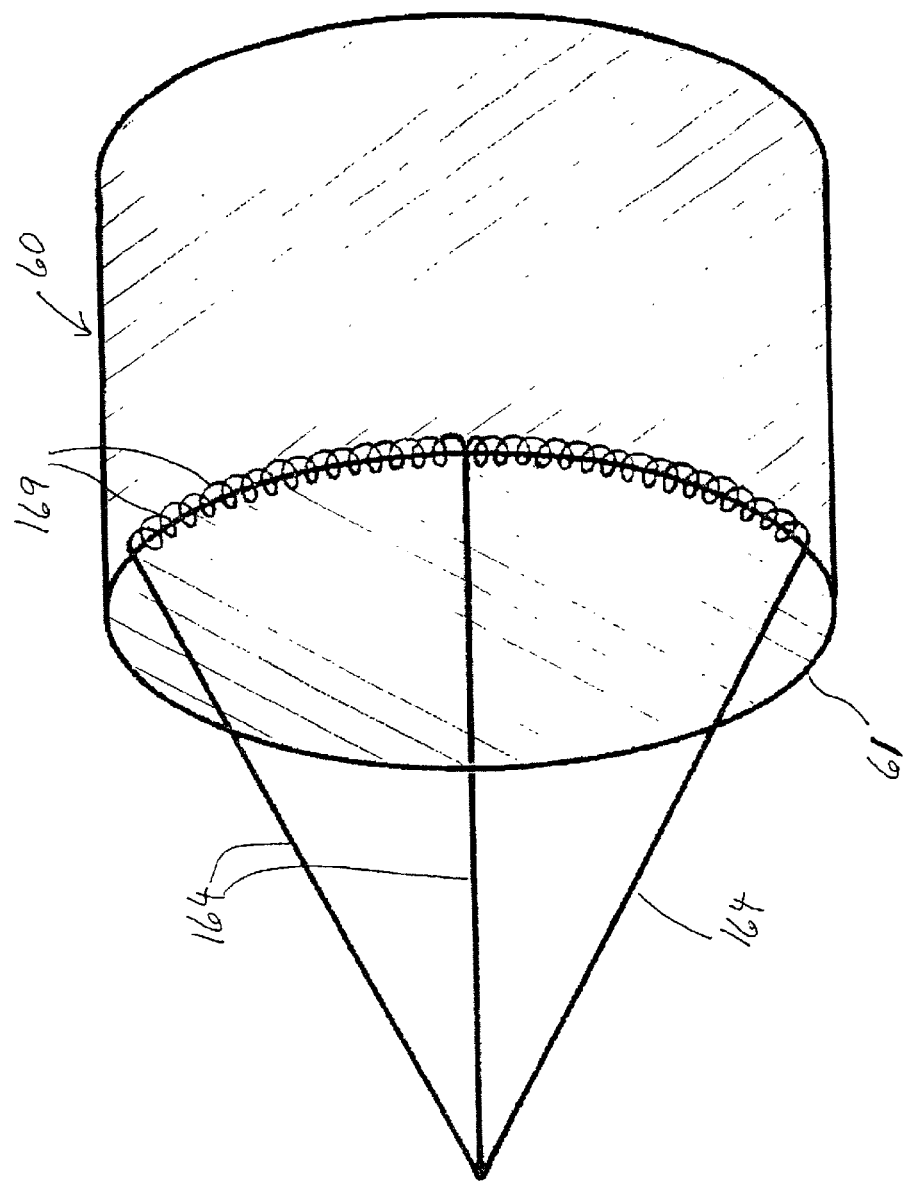
FIG. 22 is a perspective view illustrating the preferred manner of forming the tethers for the intake of the filter means.

Another aspect of the invention is illustrated in FIG. 22 illustrating an alternate form of tether or shroud 164 used to anchor filter means 60 to the guidewire. FIG. 22 illustrates that the multiple tethers 164 are formed of a single strand of material 169 which is threaded around the periphery of circular intake 61 of filter means 60 and the single strand of material 169 is used to form tethers 164. FIG. 22 shows approximately forty per cent of the circumference of intake 61 with the tethers and strand 169 applied, in the interest of clarity. In use, the full circumference carries strand 169, as well as tethers.

Figure 23:
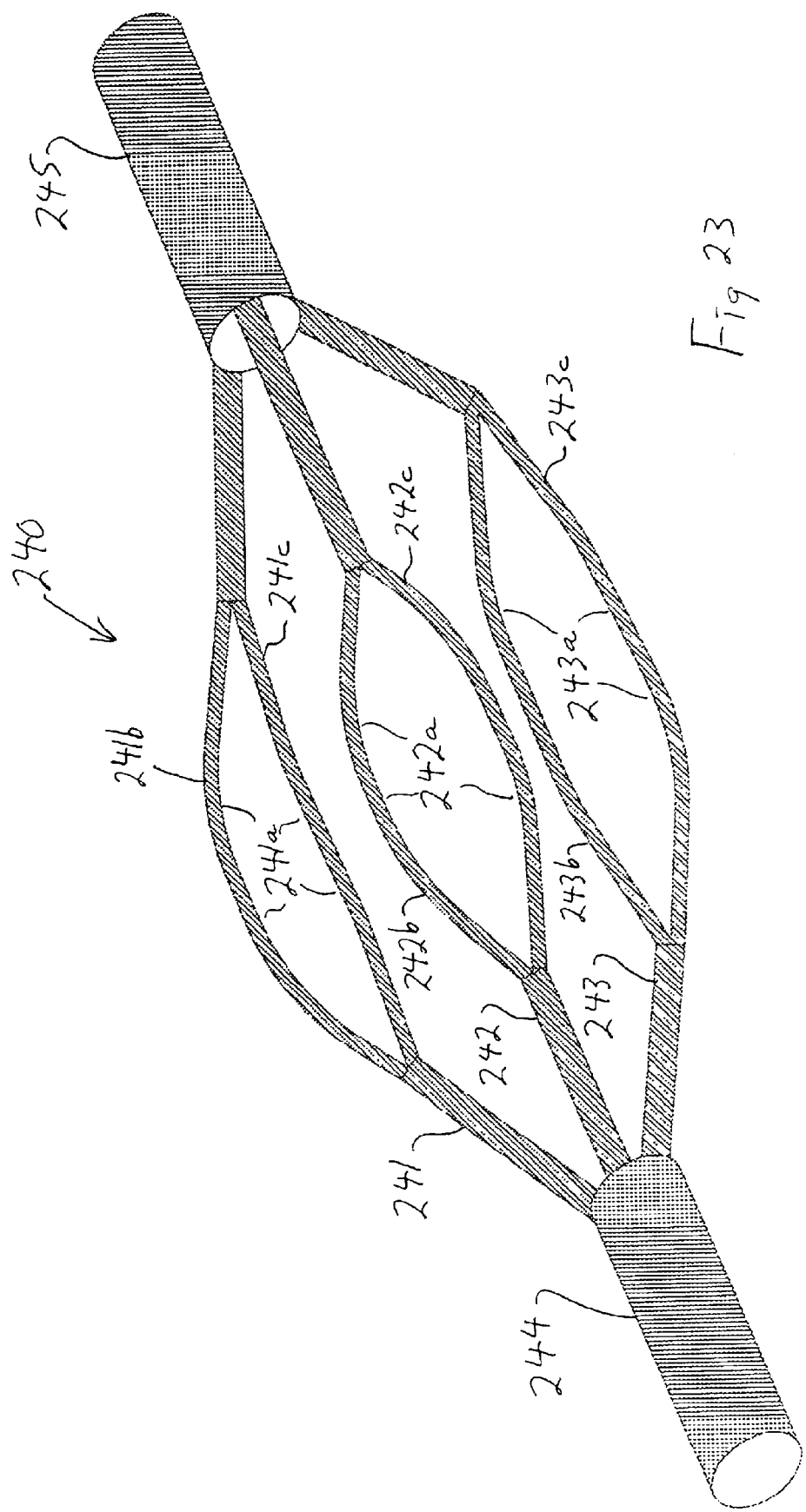
FIG. 23 is a perspective view of an alternate form of the stent.
Figure 24:
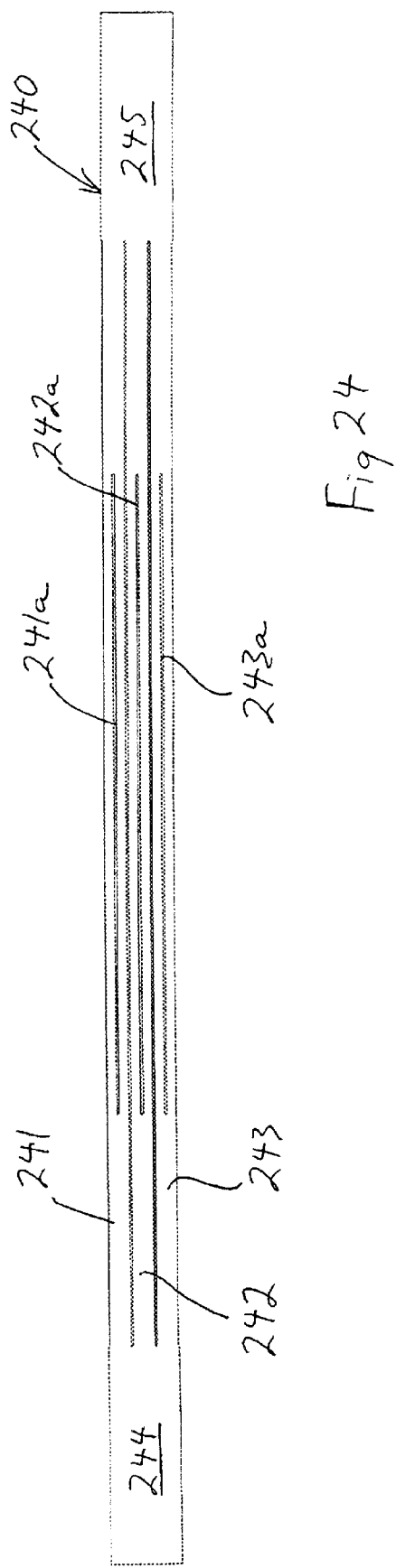
FIG. 24 is a plan view of the stent illustrated in FIG. 24 shown in layout form.

FIGS. 23 and 24 illustrate an alternate form of self-expanding stent 240. Stent 240 includes a cylindrical proximal sleeve 244, a cylindrical distal sleeve 245, and three separate arms 241, 242 and 243 extending between sleeves 244 and 245. Each of the stent arms 241–243 has a longitudinal laser cut 241a, 242a and 243a formed in the central portions, respectively. The primary purpose of the longitudinal cuts is to maximize the number of supporting arms for the intake of the filter means 60. A total of six arm segments 241b, 241c, 242b, 242c, 243b and 243c are thereby formed, which provide a circular periphery which causes the filter means to contact and seal against the artery wall. An additional purpose for the use of the longitudinal cuts in only the central portion of the longitudinal length of stent means 240 is to provide maximum self-expansion strength where the arms 241–243 bend relative to sleeves 244 and 245. Stent means 240 is rather small as far as stents go. Providing the maximum strength at the distal and proximal ends of the stent arms 241–243 assures that the stent means 240 will have the maximum ability to expand outwardly to contact the arterial wall.

FIG. 24 illustrates in layout form the design of stent means 240 as illustrated in FIG. 23. Stent means 240 includes longitudinal cuts or slots 241a, 242a and 243a.

Figure 25:
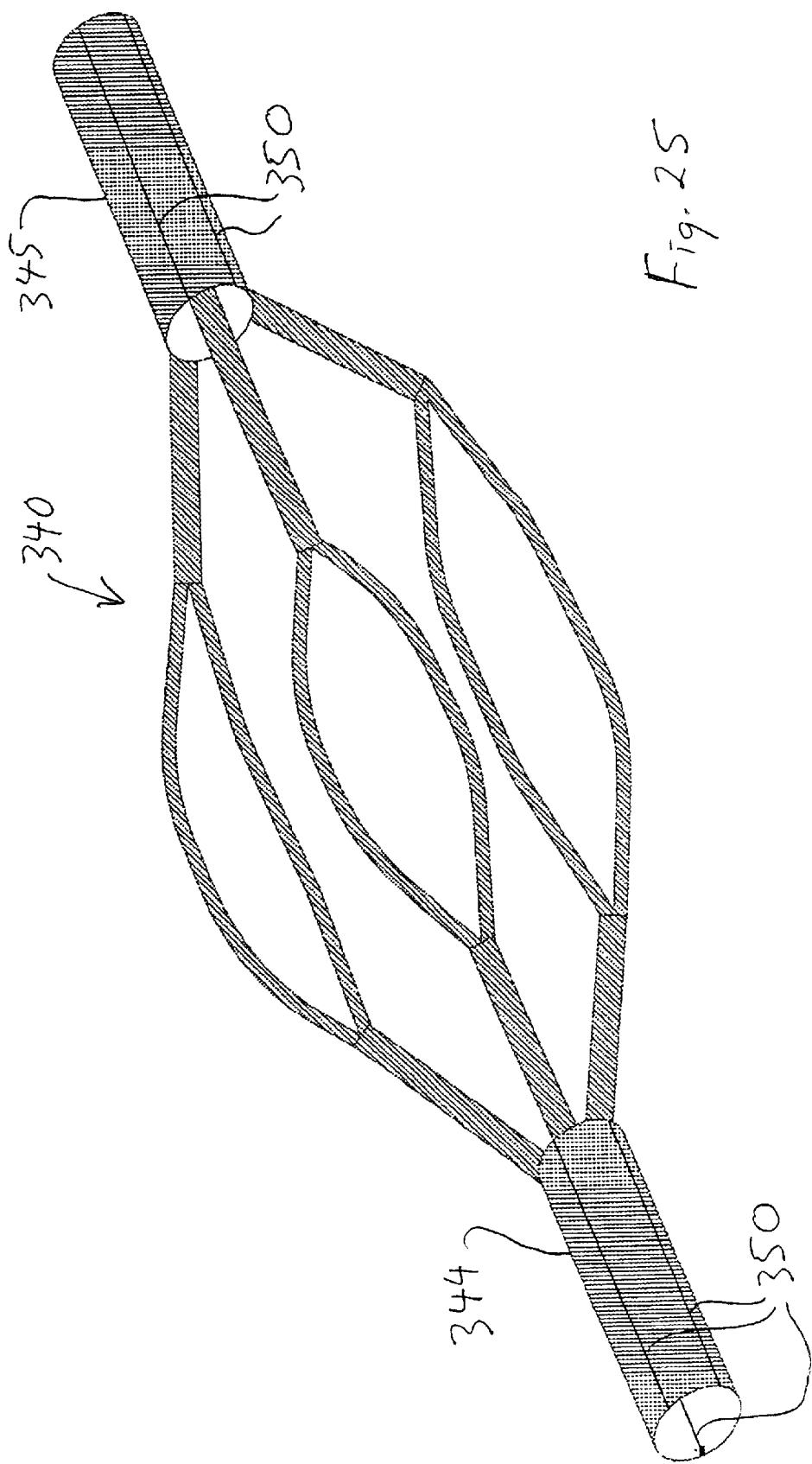
FIG. 25 is a perspective view of another self-expanding stent usable in the invention.

FIG. 25 illustrates another self-expanding stent 340, similar to stent 240, but wherein proximal end piece 344 and end piece 345 are each formed from three arcuate segments and welded together on weld lines 350. In all other respects, stent 340 is identical to stent 240.

Figure 26:
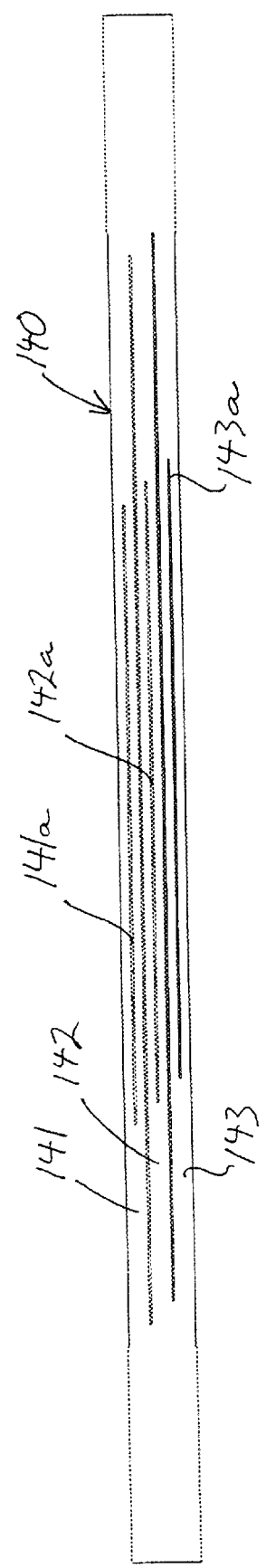
FIG. 26 is a plan view of the stent having an elliptical opening illustrated in FIGS. 13 and 14, wherein the stent is shown in its layout form.

FIG. 26 is a plan view of the alternate stent 140 illustrated in FIGS. 13 and 14 with an elliptical intake. The elliptical intake as illustrated in FIG. 14 is formed by the use of longitudinal cuts 141a, 142a and 143a that are spaced apart from each other along the longitudinal axis of stent 140.

Figure 29A:
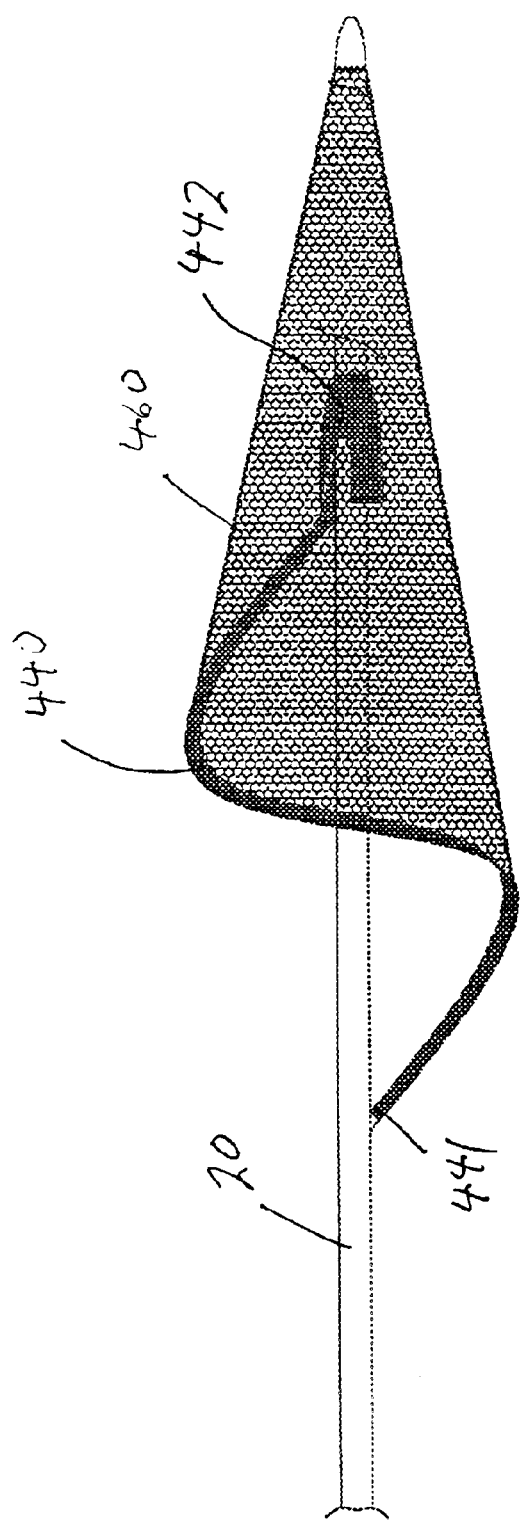
Figure 29B:
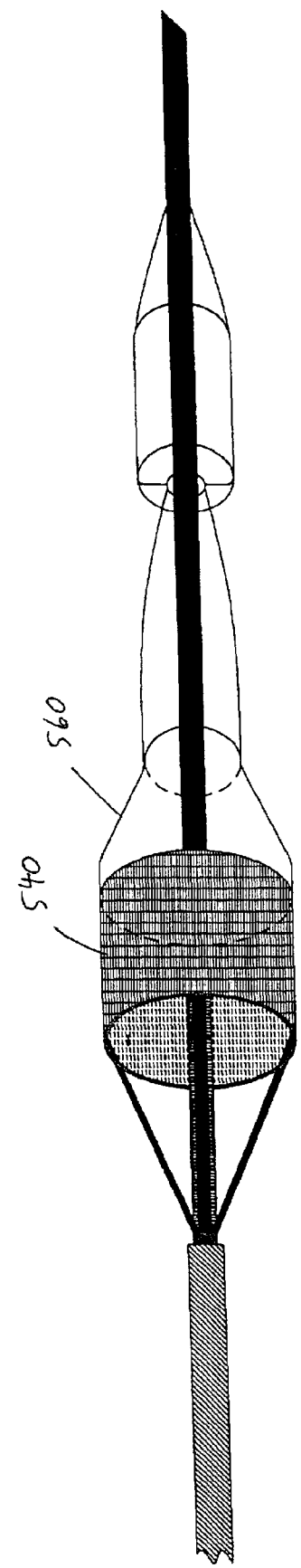

It is to be understood that various "expansion means" could be used in addition to the self-expanding stents described above. For example, FIG. 29A shows a helical expansion ring 440 that is connected to the inlet of the filter 460. Expansion ring 440 has a proximal end 441 and distal end 442. Distal end 442 is fixed to guidewire 20. Alternately, the filter 560 could have resilient, expansion material 540 embedded in its inlet as shown in FIG. 29B. FIG. 29C illustrates yet another alternate filter means 660 having an inclined "sail" 640 at its inlet. The sail 640 acts as an expansion mechanism to expand filter means 660 when exposed to arterial blood flow. FIG. 29D illustrates another form of expansion means, wherein filter 760 has its inlet coated with a hydrogel coating 740 which swells upon contact with blood and acting to expand the inlet of filter 760.

FIG. 30 illustrates another embodiment of the invention wherein guidewire 820 has a tapered distal end 821. Mounting region 830 is a recess in guidewire 820 having only one end wall, i.e., proximal end wall 831. Stent 840 is attached to guidewire 820 by a weld 850 adjacent proximal end wall 831 or other permanent connection. This embodiment has the disadvantage that stent 840 cannot "float" relative to guidewire 820.

As noted above, the alternate stents 40, 140, 240 and 340 may either be allowed to "float" on guidewire 20 between end walls 31 and 32, as shown best in FIGS. 8, 9 and 13, or it may be fixed to guidewire 20 at either its distal or proximal ends. The advantage of being able to "float" is that any inadvertent longitudinal motion or rotation of the guidewire is not immediately transmitted to the stent 40. This feature provides a level of "shock absorption" which minimizes adverse effects from unintended motion of guidewire 20. The stent is able to float by having a longitudinal length less than the longitudinal length of mounting region 30 between end walls 31 and 32, shown by clearance "x" in FIGS. 8, 9 and 13. Clearance "x" is preferably between 0.010 and 0.125 inch.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

What is claimed is:

1. A low profile emboli capture device for use in angioplasty and other intravascular procedures comprising:

a guidewire having distal and proximal ends;

said guidewire having a mounting region near said distal end, said mounting region having a cross-sectional area less than said guidewire;

a self-expanding stent carried on said guidewire at said mounting region, said self-expanding stent being movable between a retracted position and an expanded position;

a filter connected to said self-expanding stent, said filter being movable between a retracted position and an expanded position, said filter being adapted to capture emboli in its expanded position;

said self expanding stent and said filter in their retracted positions on said mounting region have a cross-sectional profile approximately the same as the cross-sectional profile of said guidewire;

a sleeve having a first position for holding said self-expanding stent and said filter against said mounting region of said guidewire, said sleeve being movable to a second position wherein said self-expanding stent and said filter are free to expand;

wherein said filter is a multi-layered mesh formed of spun, liquid polymer; and wherein said multi-layered mesh comprises fiber slumped filaments each having a width that is greater than its height.

2. A low profile emboli capture device for use in angioplasty and other intravascular procedures comprising:

a guidewire having distal and proximal ends;

said guidewire having a mounting region near said distal end, said mounting region having a cross-sectional area less than said guidewire;

a self-expanding stent carried on said guidewire at said mounting region, said self-expanding stent being movable between a retracted position and an expanded position;

a filter connected to said self-expanding stent, said filter be movable between a retracted position and an expanded position, said filter being adapted to capture emboli in its expanded position;

said self expanding stent and said filter in their retracted positions on said mounting region have a cross-sectional profile approximately the same as the cross-sectional profile of said guidewire;

a sleeve having a first position for holding said self-expanding stent and said filter against said mounting region of said guidewire, said sleeve being movable to a second position wherein said self-expanding stent and said filter are free to expand; and wherein said sleeve is slidable on said guidewire and includes an inverted, double folded end portion extending over said self-expanding stent and said filter, so that as said sleeve is moved from said first position to said second position, it releases said self-expanding stent and said filter without frictional movement between said sleeve and said filter.

3. A low profile emboli capture device for use in angioplasty and other intravascular procedures comprising:

a guidewire having distal and proximal ends;

said guidewire having a mounting region near said distal end, said mounting region having a cross-sectional area less than said guidewire;

a self-expanding stent carried on said guidewire at said mounting region, said self-expanding stent being movable between a retracted position and an expanded position;

a filter connected to said self-expanding stem, said filter being movable between a retracted position and an expanded position, said filter being adapted to capture emboli in its expanded position;

said self expanding stent and said filter in their retracted positions on said mounting region have a cross-sectional profile approximately the same as the cross-sectional profile of said guidewire;

a sleeve having a first position for holding said self-expanding stent and said filter against said mounting region of said guidewire, said sleeve being movable to a second position wherein said self-expanding stent and said filter are free to expand; and wherein said self-expanding stent and said filter are moved from their expanded positions to their retracted positions by advancing a catheter in a distal direction to compress said stent against said guidewire.

4. A low profile emboli capture device for use in angioplasty and other intravascular procedures comprising:

a guidewire having distal and proximal ends;

said guidewire having a mounting region near said distal end, said mounting region having a cross-sectional area less than said guidewire;

a self-expanding stent carried on said guidewire at said mounting region, said self-expanding stent being movable between a refracted position and an expanded position;

a filter connected to said self-expanding stent, said filter being movable between a retracted position and an expanded position, said filter being adapted to capture emboli in its expanded position;

said self expanding stent and said filter in their retracted positions on said mounting region have a cross-sectional profile approximately the same as the cross-sectional profile of said guidewire;

a sleeve having a first position for holding said self-expanding stent and said filter against said mounting region of said guidewire, said sleeve being movable to a second position wherein said self-expanding stent and said filter are free to expand; and wherein said sleeve is imperforate except for plurality of openings formed near its distal end, through which lubricants or medications may be applied to the blood vessel in which the device is utilized.

5. A low profile emboli capture device for use in angioplasty and other intravascular procedures comprising:
  a guidewire having distal and proximal ends;
  said guidewire having a mounting region near said distal end, said mounting region having a cross-sectional area less than said guidewire;
  a self-expanding stent carried on said guidewire at said mounting region, said self-expanding stent being movable between a retracted position and an expanded position;
  a filter connected to said self-expanding stent, said filter being movable between a retracted position and en expanded position, said filter being adapted to capture emboli in its expanded position;
  said self expanding stent and said filter in their retracted positions on said mounting region have a cross-sectional profile approximately the same as the cross-sectional profile of said guidewire;
  a sleeve having a first position for holding said self-expanding stent and said filter against said mounting region of said guidewire, said sleeve being movable to a second position wherein said self-expanding stent and said filter are free to expand;
  wherein said sleeve is slidable and further comprising a sleeve handle bonded to said sleeve for moving said sleeve on said guidewire; and
  wherein said sleeve handle comprises two parts pivotally connected to each other and movable between a closed position and an open position, and in said open position, said sleeve is split apart for quick removal from said guidewire.

6. A low profile emboli capture device for use in angioplasty and other intravascular procedures comprising:
  a guidewire having distal and proximal ends;
  said guidewire having a mounting region near said distal end, said mounting region having a cross-sectional area less than said guidewire;
  a self-expanding stent carried on said guidewire at said mounting region, said self-expanding stent being movable between a retracted position and an expanded position;
  a filter connected to said self-expanding stent, said filter being movable between a retracted position and an expanded position, said filter being adapted to capture emboli in its expanded position;
  said self expanding stent and said filter in their retracted positions on said mounting region have a cross-sectional profile approximately the same as the cross-sectional profile of said guidewire;
  a sleeve having a first position for holding said self-expanding stent and said filter against said mounting region of said guidewire, said sleeve being movable to a second position wherein said self-expanding stent and said filter are free to expand; and
  wherein said sleeve has its distal end crumpled to facilitate application of said sleeve over said mounting region of said guidewire.

7. A low profile emboli capture device for use in angioplasty and other intravascular procedures comprising:
  a guidewire having distal and proximal ends;
  said guidewire having a mounting region near said distal end, said mounting region having a cross-sectional area less than said guidewire;
  a self-expanding stent carried on said guidewire at said mounting region, said self-expanding stent being movable between a retracted position and an expanded position;
  a filter connected to said self-expanding stent said filter being movable between a retracted position and an expanded position, said filter being adapted to capture emboli in its expanded position;
  said self expanding stent and said filter in their retracted positions on said mounting region have a cross-sectional profile approximately the same as the cross-sectional profile of said guidewire;
  a sleeve having a first position for holding said self-expanding stent and said filter against said mounting region of said guidewire, said sleeve being movable to a second position wherein said self-expanding stent and said filter are free to expand; and
  wherein said sleeve has a spring carried at its distal end to facilitate application of said sleeve over said mounting region of said guidewire.

8. A low profile emboli capture device for use in angioplasty and other intravascular procedures comprising:
  a guidewire having distal and proximal ends;
  said guidewire having a mounting region near said distal end, said mounting region having a cross-sectional area less than said guidewire;
  a self-expanding stent carried on said guidewire at said mounting region, said self-expanding stent being movable between a retracted position and an expanded position;
  a filter connected to said self-expanding stent, said filter being movable between a retracted position and an expanded position, said filter being adapted to capture emboli in its expanded position;
  said self expanding stent and said filter in their retracted positions on said mounting region have a cross-sectional profile approximately the same as the cross-sectional profile of said guidewire;
  a sleeve having a first position for holding said self-expanding stent and said filter against said mounting region of said guidewire, said sleeve being movable to a second position wherein said self-expanding stent and said filter are free to expand; and
  wherein said sleeve includes a first section separately applied over said mounting region of said guidewire, a second section adapted to slide upon said guidewire at its proximal end and to slide over said first section, and said first and second sections each having distal ends, the distal ends being connected.

9. A low profile emboli capture device for use in angioplasty and other intravascular procedures comprising:
  a guidewire having distal and proximal ends;
  said guidewire having a mounting region near said distal end, said mounting region having a cross-sectional area less than said guidewire;
  a self-expanding stent carried on said guidewire at said mounting region, said self-expanding stent being movable between a retracted position and an expanded position;
  a filter connected to said self-expanding stent, said filter being movable between a retracted position and an expanded position, said filter being adapted to capture emboli in its expanded position;
  said self expanding stent and said filter in their retracted positions on said mounting region have a cross-sectional profile approximately the same as the cross-sectional profile of said guidewire;
  a sleeve having a first position for holding said self-expanding stent and said filter against said mounting region of said guidewire, said sleeve being movable to a second position wherein said self-expanding stent and said filter are free to expand; and wherein said guidewire includes a sleeve retaining groove formed in said guidewire near the proximal end of said mounting region, and wherein said sleeve carries a spring loaded collar at its distal end, said spring loaded collar adapted to seat in said sleeve retaining groove.

10. The device of claim 9 wherein said mounting region of said guidewire has a smaller cross-section that the proximal end of said guidewire, said smaller cross-section extends to the distal end of said guidewire, and said self-expanding stent is adapted to be slid onto said distal end of said guidewire.

11. The device of claim 10 further comprising a cylindrical ring adapted to slide onto the distal end of said guidewire and member for permanently attaching said ring to said guidewire.

12. A low profile emboli capture device for use in angioplasty and other intravascular procedures comprising:

a guidewire having distal and proximal ends;

said guidewire having a mounting region near said distal end, said mounting region having a cross-sectional area less than said guidewire;

a self-expanding stent carried on said guidewire at said mounting region, said self-expanding stent being movable between a refracted position and an expanded position;

a filter connected to said self-expanding stent, said filter being movable between a retracted position and an expanded position, said filter being adapted to capture emboli in its expanded position;

said self expanding stent and said filter in their retracted positions on said mounting region have a cross-sectional profile approximately the same as the cross-sectional profile of said guidewire;

a sleeve having a first position for holding said self-expanding stent and said filter against said mounting region of said guidewire, said sleeve being movable to a second position wherein said self-expanding stern and said filter are free to expand; and wherein said self-expanding stent comprises a plurality of longitudinal members wherein each of said members has a longitudinal cut formed between its proximal and distal ends.

13. A low profile emboli capture device for use in angioplasty and other intravascular procedures comprising:

a guidewire having distal and proximal ends;

said guidewire having a mounting region near said distal end, said mounting region having a cross-sectional area less than said guidewire;

an expansion member carried on said guidewire at said mounting region, said expansion member being moveable between a retracted position and an expanded position;

a filter connected to said expansion member, said filter being movable between a retracted position and an expanded position said filter being adapted to capture emboli in its expanded position;

said expansion member and filter in their retracted positions on said mounting region have a cross-sectional profile approximately the same as the cross-sectional profile of said guidewire; and a sleeve having a first position for holding said expansion member and said filter against said mounting region of said guidewire, said sleeve being movable along said guidewire to a second position wherein said expansion member and said filter are free to expand, and including an inverted, double folded end portion extending over said expansion and filter.

\* \* \* \* \*

UNITED STATES PATENT AND TRADEMARK OFFICE
CERTIFICATE OF CORRECTION

PATENT NO. : 6,840,950 B2
DATED : January 11, 2005
INVENTOR(S) : Ulf Harry Stanford et al.

It is certified that error appears in the above-identified patent and that said Letters Patent is hereby corrected as shown below:

Column 11,
Line 58, delete "be" and insert -- being --

Column 12,
Line 22, delete "stem" and insert -- stent --
Line 48, delete "refracted" and insert -- retracted --

Column 13,
Line 12, delete "en" and insert -- an --

Column 15,
Line 28, delete "refracted" and insert -- retracted --

Column 16,
Line 4, delete "stern" and insert -- stent --

Signed and Sealed this

Thirty-first Day of May, 2005

JON W. DUDAS
*Director of the United States Patent and Trademark Office*